United States Patent
Wynn et al.

(10) Patent No.: US 8,124,806 B2
(45) Date of Patent: *Feb. 28, 2012

(54) CONTRAST AGENTS

(75) Inventors: Duncan Wynn, Amersham (GB);
Robert James Domett Nairne, St. Albans (GB); Oskar Axelsson, Oslo (NO); Mikkel Thaning, Oslo (NO); Nicolas Lasbistes, Amersham (GB)

(73) Assignee: GE Healthcare AS, Oslo (NO)

( * ) Notice: Subject to any disclaimer, the term of this patent is extended or adjusted under 35 U.S.C. 154(b) by 863 days.

This patent is subject to a terminal disclaimer.

(21) Appl. No.: 12/279,100

(22) PCT Filed: Feb. 14, 2007

(86) PCT No.: PCT/NO2007/000051
§ 371 (c)(1),
(2), (4) Date: Aug. 12, 2008

(87) PCT Pub. No.: WO2007/094683
PCT Pub. Date: Aug. 23, 2007

(65) Prior Publication Data
US 2009/0053142 A1 Feb. 26, 2009

(30) Foreign Application Priority Data
Feb. 15, 2006 (NO) .................................. 20060724

(51) Int. Cl.
*C07C 233/65* (2006.01)
*A61K 49/00* (2006.01)
(52) U.S. Cl. ..................................... 564/153; 424/9.452
(58) Field of Classification Search .................. 564/153; 424/9.452
See application file for complete search history.

(56) References Cited

U.S. PATENT DOCUMENTS
5,817,873 A 10/1998 Meyer et al.

FOREIGN PATENT DOCUMENTS
DE 2039214 2/1971
EP 0782563 6/1999
WO 95/01966 1/1995

OTHER PUBLICATIONS
PCT/NO2007/000051 Int'l Search Report dated Jul. 2007.

*Primary Examiner* — Shailendra Kumar

(57) ABSTRACT

The present invention relates to a class of compounds and to diagnostic compositions containing such compounds where the compounds are iodine containing compounds. More specifically the iodine containing compounds are chemical compounds containing an aliphatic central moiety containing amide functions allowing for the arrangement of three iodinated phenyl groups bound thereto. The invention also relates to the use of such diagnostic compositions as contrast agents in diagnostic imaging and in particular in X-ray imaging and to contrast media containing such compounds.

20 Claims, No Drawings

CONTRAST AGENTS

This application is a filing under 35 U.S.C. 371 of international application number PCT/NO2007/000051, filed Feb. 14, 2007, which claims priority to application number 20060724 filed Feb. 15, 2006, in Norway the entire disclosure of which is hereby incorporated by reference.

TECHNICAL FIELD OF THE INVENTION

The present invention relates to a class of compounds and to diagnostic compositions containing such compounds where the compounds are iodine containing compounds. More specifically the iodine containing compounds are chemical compounds containing an aliphatic central moiety containing amide functions allowing for the arrangement of three iodinated phenyl groups bound thereto.

The invention also relates to the use of such diagnostic compositions as contrast agents in diagnostic imaging and in particular in X-ray imaging and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade name Gastrografen™), ionic dimers such as ioxaglate (marketed e.g. under the trade name Hexabrix™), nonionic monomers such as isohexyl (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™).

The most widely used commercial non-ionic X-ray contrast agents such as those mentioned above are considered safe. Contrast media containing iodinated contrast agents are used in more that 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered, and by the ease of storage and ease of administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in g iodine per ml of the formulated contrast medium for administration). The iodinated contrast agent must also be completely soluble in the formulation medium, usually an aqueous medium, and remain in solution during storage.

The osmolalities of the commercial products, and in particular of the non-ionic compounds is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable. The osmolality is a function of the number of particles per volume unit of the formulated contrast medium.

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(tri-iodophenyl) dimers such as iodixanol (EP patent 108638) has provided contrast media with reduced osmotoxicity allowing contrast effective iodine concentration to be achieved with hypotonic solution, and has even allowed correction of ionic imbalance by inclusion of plasma ions while still maintaining the contrast medium Visipaque™ at the desired osmolality (WO 90/01194 and WO 91/13636).

The X-ray contrast media at commercial high iodine concentration have relative high viscosity, ranging from about 15 to about 60 mPas at ambient temperature. Generally, contrast media where the contrast enhancing agent is a dimer has higher viscosity than the corresponding contrast media where the contrast enhancing agent is the monomer corresponding to the dimer. Such high viscosities may pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast agents of high molecular weight has been proposed, e.g. polymers with substituted triiodinated phenyl groups grafted on the polymer, see EP 354836, EP 436316 and U.S. Pat. No. 5,019,370. Further, WO 9501966, EP 782563 and U.S. Pat. No. 5,817,873 read on compounds having e.g. 3 and 4 substituted triiodinated phenyl groups arranged linearly or around a central core. However, none of these proposed compounds are on the market.

Hence there still exists a desire to develop contrast agents that solves one or more of the problems discussed above. Such agents should ideally have improved properties over the soluble iodine containing compounds on the market in one or more of the following properties: renal toxicity, osmolality, viscosity, solubility, injection volumes/iodine concentration and attenuation/radiation dose.

SUMMARY OF THE INVENTION

The present invention provides compounds useful as contrast media having improved properties over the known media with regards to at least one of the following criteria osmolality (and hence the renal toxicity), viscosity, iodine concentration and solubility. The contrast media comprises iodine containing contrast enhancing compounds where iodine containing compounds are chemical compounds containing a central aliphatic moiety, allowing for the arrangement of three iodinated phenyl groups bound to thereto through linker groups containing amide functions. The iodine containing contrast enhancing compounds can be synthesized from commercially available and relatively inexpensive starting materials.

DETAILED DESCRIPTION OF THE INVENTION

The new compounds of the invention, their use as X-ray contrast agents, their formulation and production are specified in the attached claims and in the specification hereinafter.

The contrast enhancing compounds are synthetic chemical compounds of formula (I)

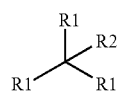

Formula (I)

wherein each $R^1$ independently are the same or different and denote a moiety —$(CX_2)_n$—$R^3$—R;
$R^2$ denote hydrogen atom, hydroxyl group or a $C_1$-$C_4$ alkyl group where the alkyl group may be substituted by hydroxyl and amino groups and interrupted by an oxygen atom;

each $R^3$ independently are the same or different and denote a moiety of formula —$NR^5$—CO— wherein $R^5$ has the meaning of $R^2$;
X denotes hydrogen and hydroxyl;
n is a integer of 1 to 4; and
each R independently are the same or different and denote a triiodinated phenyl group, preferably a 2,4,6-triiodinated phenyl group further substituted by two groups $R^4$ wherein each $R^4$ are the same or different and denote a hydrogen atom or a non-ionic hydrophilic moiety, provided that at least one $R^4$ group in the compound of formula (I) is a hydrophilic moiety;
and salts or optical active isomers thereof.

The substituents $R^1$ above are the same or different. Preferably X denotes a hydrogen atom and $R^1$ then denote the moiety —$(CH_2)_n$—$R^3$—R. It is also preferred that each of the $R^3$ groups are the same and denote moiety of formula —$NR^5$—CO— wherein $R^5$ has the meaning of $R^2$. The $R^1$ moieties will then be of the formula —$(CH_2)_n$—$NR^5$—CO—R. Even more preferred $R^5$ denotes hydrogen thus $R^3$ denotes the amide residue —NH—CO— linking the group R to the central alkyl moiety. In a particularly preferred aspect of the invention, n denotes the integer of 1 to 3.

It is further preferred that the substituent $R^2$ of the compound of formula (I) denotes a hydrogen atom or a methyl group and specifically preferred $R^2$ denotes a hydrogen atom.

Each of the iodinated R groups can be the same or different and preferably denote a 2,4,6-triiodinated phenyl group, further substituted by two groups $R^4$ in the remaining 3 and 5 positions in the phenyl moiety.

The non-ionic hydrophilic moieties may be any of the non-ionizing groups conventionally used to enhance water solubility. Hence, the $R^4$ substituents may be the same or different and shall preferably all denote a non-ionic hydrophilic moiety comprising esters, amides and amine moieties, optionally further substituted by a straight chain or branched chain $C_{1-10}$ alkyl groups, preferably $C_{1-5}$ alkyl groups, where the alkyl groups also may have one or more $CH_2$ or CH moieties replaced by oxygen or nitrogen atoms. The $R^4$ substituents may also further contain one or more groups selected from oxo, hydroxyl, amino or carboxyl derivative, and oxo substituted sulphur and phosphorus atoms. Each of the straight or branched alkyl groups preferably contain 1 to 6 hydroxy groups and more preferably 1 to 3 hydroxy groups. Therefore, in a further preferred aspect, the $R^4$ substituents are the same or different and are polyhydroxy $C_{1-5}$ alkyl, hydroxyalkoxyalkyl with 1 to 5 carbon atoms and hydroxypolyalkoxyalkyl with 1 to 5 carbon atoms, and are attached to the iodinated phenyl group via an amide or a carbamoyl linkage.

The $R^4$ groups of the formulas listed below are particularly preferred:
—CONH—$CH_2$—$CH_2$—OH
—CONH—$CH_2$—CHOH—$CH_2$—OH
—CON($CH_3$)$CH_2$—CHOH—$CH_2$OH
—CONH—CH—$(CH_2$—OH$)_2$
—CON—$(CH_2$—$CH_2$—OH$)_2$
—$CONH_2$
—$CONHCH_3$
—$NHCOCH_2$OH
—N($COCH_3$)H
—N($COCH_3$)$C_{1-3}$ alkyl
—N($COCH_3$)— mono, bis or tris-hydroxy $C_{1-4}$ alkyl
—N($COCH_2$OH)— hydrogen, mono, bis or tris-hydroxy $C_{1-4}$ alkyl N(CO—CHOH—$CH_2$OH)— hydrogen, mono, bis or trihydroxylated $C_{1-4}$ alkyl.

—N(CO—CHOH—CHOH—CH$_2$OH)— mono, bis or trihydroxylated C$_{1-4}$ alkyl
—N(COCH$_2$OH)$_2$
—CON(CH$_2$—CHOH—CH$_2$—OH)(CH$_2$—CH$_2$—OH)
—CONH—C(CH$_2$—OH)$_3$ and
—CONH—CH(CH$_2$—OH)(CHOH—CH$_2$—OH).

Even more preferably the R$^4$ groups will be equal or different and denote one or more moieties of the formulas —CONH—CH$_2$—CHOH—CH$_2$—OH, —CON(CH$_3$)CH$_2$—CHOH—CH$_2$OH, —CONH—CH—(CH$_2$—OH)$_2$, —CON—(CH$_2$—CH$_2$—OH)$_2$, —CONH—CH$_2$—CHOH—CH$_2$—OH, —NHCOCH$_2$OH, —NHCO—CHOH—CH$_2$OH, —NHCO—CHOH—CHOH—CH$_2$OH and —N(COCH$_2$OH)— mono, bis or tris-hydroxy C$_{1-4}$ alkyl, and even more preferably all R groups are the same and the R$^4$ groups in each R are different and denote —CONH—CH$_2$—CHOH—CH$_2$—OH, CON(CH$_3$)CH$_2$—CHOH—CH$_2$OH, —NHCO—CHOH—CH$_2$OH, —NHCO—CHOH—CHOH—CH$_2$OH and —NHCOCH$_2$OH.

Most preferably all substituents R$^1$ in formula (I) are equal.

Thus, preferred structures according to the invention include the compounds of formula (II):

Formula (II)

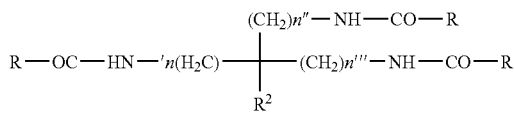

In formula (II), each group R has the meaning above, more preferably each iodophenyl groups R are the same and the R$^4$ groups all denote non-ionic hydrophilic moieties. The group R$^{2'}$ denotes a hydrogen or a methyl group, most preferably a hydrogen atom. n', n" and n'" are the same or different and denotes integers of 1, 2 or 3.

Some preferred examples the structures according to the invention include the compounds of formulas (IIIa), (IIIb), (IIIc) IIId) and (IIIe) below.

Formula (IIIa)

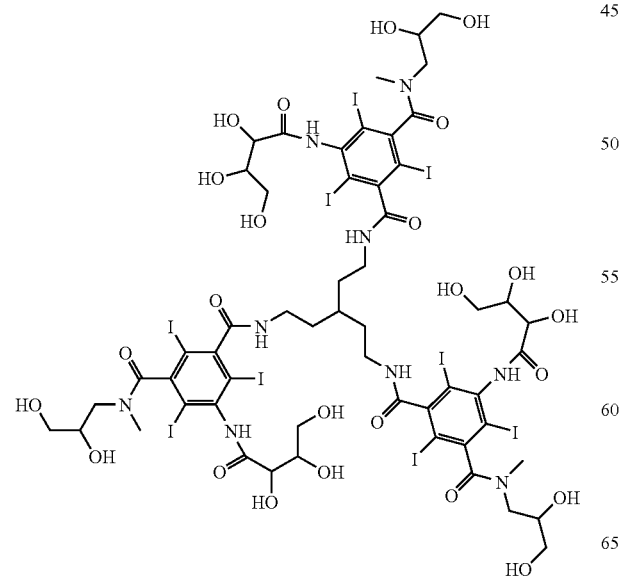

Formula (IIIb)

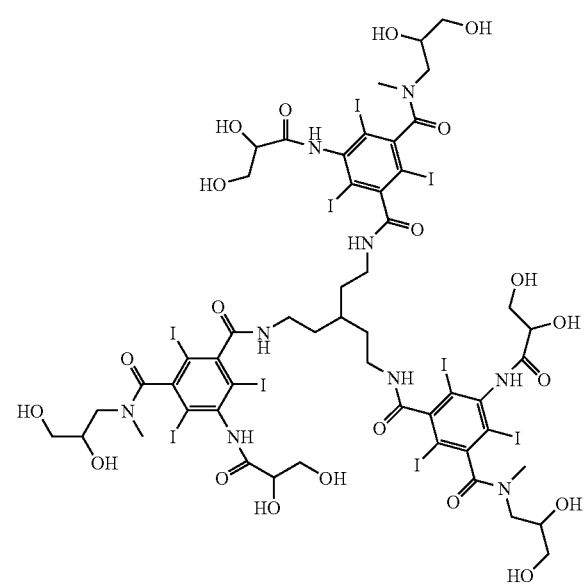

Formula (IIIc)

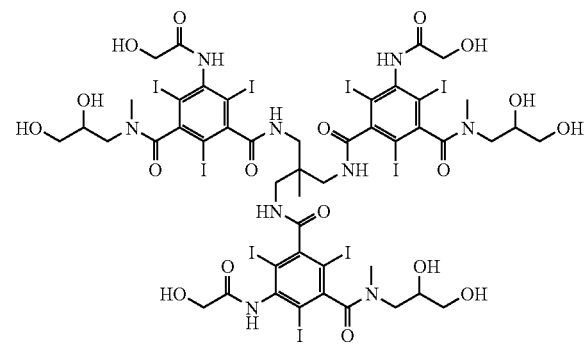

Formula (IIId)

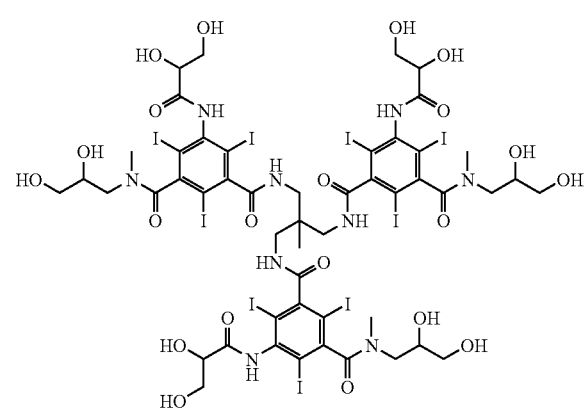

Formula (IIIe)

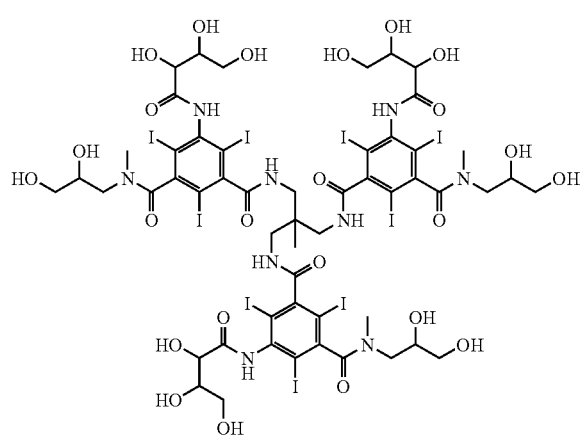

The compounds of formula (I) will attain a relatively compact, folded conformation. Such conformation are relatively round and globular form such as a star-form with the relatively bulky iodinated phenyl substituents filling up the area between the 3 arms of the star or a "stacked spoon" form where the iodinated phenyl groups are aligned as the spoon "bowls" in a stack of spoons. Globular molecules will usually have enhanced solubility compared with similar molecules with a more planar structure and also have lower viscosities.

At an iodine concentration of 320 mg/ml, which is a common concentration for commercially available iodinated contrast media, the concentration of the compound of formula (I) will be approximately 0.28 M (Molar). The contrast medium will also be hypoosmolar at this iodine concentration, and this is an advantageous property with regards to the nephrotoxicity of the contrast medium. It is also possible to add electrolytes to the contrast medium to lower the cardiovascular effects as explained in WO 90/01194 and WO 91/13636.

Compounds of formula (I) also comprises optical active isomers. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic composition comprising a compound of formula (I) as described above together with at least one physiologically tolerable carrier or excipient, e.g. in aqueous solution for injection optionally together with added plasma ions or dissolved oxygen.

The contrast agent composition of the invention may be in a ready to use concentration or may be a concentrate form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast media which are administered by injection or infusion, the desired upper limit for the solution's viscosity at ambient temperature (20° C.) is about 30 mPas, however viscosities of up to 50 to 60 mPas and even more than 60 mPas can be tolerated. For contrast media given by bolus injection, e.g. in angiographic procedures, osmotoxic effects must be considered and preferably the osmolality should be below 1 Osm/kg $H_2O$, preferably below 850 mOsm/kg $H_2O$ and more preferably about 300 mOsm/kg $H_2O$.

With the compounds of the invention such viscosity, osmolality and iodine concentrations targets can be met. Indeed, effective iodine concentrations can be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/01194 and WO 91/13636.

In particular, addition of sodium and calcium ions to provide a contrast medium isotonic with blood for all iodine concentrations is desirable and obtainable. The plasma cations may be provided in the form of salts with physiologically tolerable counterions, e.g. chloride, sulphate, phosphate, hydrogen carbonate etc., with plasma anions preferably being used.

In a further embodiment the invention provides diagnostic agents comprising a compound of formula (I) and diagnostic compositions comprising a compound of formula (I) together with pharmaceutically acceptable carriers or excipients. The diagnostic agents and composition are preferably for use in X.ray diagnosis.

Hence, the invention further embraces use of a diagnostic agent and a diagnostic composition containing a compound of formula (I) in X-ray contrast examinations and use of a compound of formula (I) for the manufacture of a diagnostic composition for use as an X-ray contrast agent.

A method of diagnosis comprising administration of compounds of formula (I) to the human or animal body, examining the body with a diagnostic device and compiling data from the examination is also provided. In the method of diagnosis the body may also be preadministrated with compounds of formula (I).

Furthermore, a method of imaging, specifically X-ray imaging is provided, which comprises administration of compounds of formula (I) to the human or animal body, examining the body with a diagnostic device and compiling data from the examination and optionally analysing the data. In the method of imaging the body may also be preadministrated with compounds of formula (I).

The compounds of the general formula (I) can be synthesized by multistep procedures from starting materials that are either known from the state of art or that are commercially available. Tri-iodinated phenyl groups R and precursors thereof are commercially available or can be produced following procedures described or referred to e.g. in WO95/35122 and WO98/52911. 5-amino-2,4,6-triiodo-isophtalic acid for example is available e.g. from Aldrich and 5-amino-2,4,6-triiodo-N,N'-bis(2,3-dihydroxypropyl)-isophthalamide is commercially available e.g. from Fuji Chemical Industries, Ltd.

Alkyl-amines are likewise commercially available or readily synthesized from available starting materials. 2-aminomethyl-propane-1,3-diamine is e.g. prepared according to procedure described in Journal of Organic chemistry, 1946, 11, pp. 736-740 and the (2-Amino-ethyl)-pentane-1,5-diamine preparation is described in WO2003006070A2. 4-(3-Amino-propyl)-heptane-1,7-diamine (8) can be preparation as described in Hahn & Tamm, Angew. Chem., Int. Ed. Engl., 1992, 31(9), 1212-14. Assymetric triamines can be prepared according to synthesis described in the literature, e.g.

Hara, Yoshinori; Takahashi, Hiroko. Preparation of 3-aminomethyl-1,6-diaminohexane. Jpn. Kokai Tokkyo Koho (1998), 5 pp. CODEN: JKXXAF JP 10045681 A 19980217 Heisei. CAN 128:180152 AN 1998:108114 CAPLUS;

Bischof, Eric; Dahmer, Juergen; Flink, Andreas; Krohn, Wolfgang; Molnar, Attila. Process for the preparation of triisocyanates. Eur. Pat. Appl. (1996), 6 pp. CODEN: EPXXDW EP 749958 A1 19961227 CAN 126:131881 AN 1997:121326 CAPLUS;

Castle, John E. 1,6-Hexanediamine derivatives. (1950), U.S. Pat. No. 2,532,277 19501205 CAN 45:19191 AN 1951:19191 CAPLUS;

Castle, John E. 1,6-Hexanediamine derivatives. (1950), U.S. Pat. No. 2,532,277 19501205 CAN 45:19191 AN 1951:19191 CAPLUS;

Cuthbertson, Alan; Solbakken, Magne; Bjurgert, Emma. Preparation of radiolabeled sulfonamide hydroxamate matrix metalloproteinase inhibitors as imaging agents. PCT Int. Appl. (2005), 79 pp. CODEN: PIXXD2 WO 2005049005 A1 20050602 CAN 143:26884 AN 2005:471932 CAPLUS;

Weigert, F. J. Polyamines from cyanobutadienes. Journal of Organic Chemistry (1978), 43(4), 622-6. CODEN: JOCEAH ISSN: 0022-3263. CAN 88:89574 AN 1978:89574 CAPLUS; and Geissman, T. A.; Schlatter, Maurice J.; Webb, Irving D. The preparation of 1,3-diamino-2-methylaminopropane and 1,3-diamino-2-(aminomethyl)propane. Journal of Organic Chemistry (1946), 11 736-40. CODEN: JOCEAH ISSN: 0022-3263. CAN 41:7870 AN 1947:7870 CAPLUS Alkylamines used as starting materials in the synthesis of compounds of formula (I) can also be prepared according to the following synthetic procedures A and B:

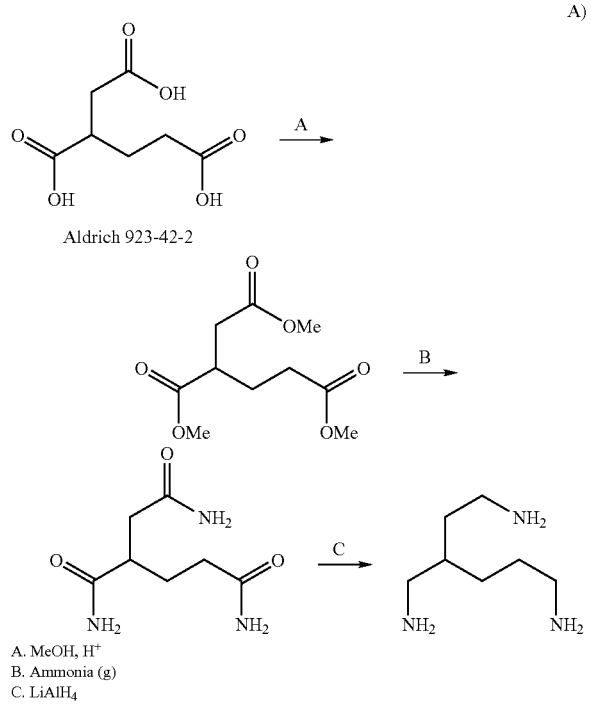

A. MeOH, H+
B. Ammonia (g)
C. LiAlH4

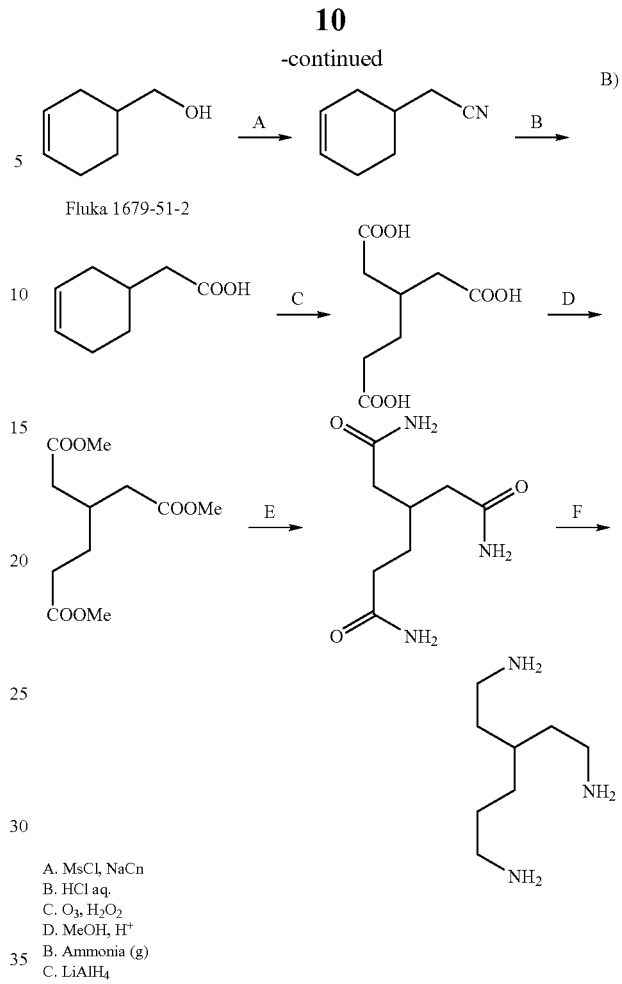

A. MsCl, NaCn
B. HCl aq.
C. O3, H2O2
D. MeOH, H+
B. Ammonia (g)
C. LiAlH4

To synthesize compounds of formula (I), the $R^4$ groups or precursors thereof denoted $R^{4'}$ on the R group are protected and a reactive substituent is formed that is brought to react with an alkyl-triamine of formula C $[(CX_2)_n—NHR^5]_3$. Suitable, the reactive functionality on the R-group can be a group containing an acid chloride function. The $R^{4'}$ precursor groups can be deprotected and/or completed after the trimeric product is formed. The procedure is explained in detail in the following and involves the following steps:

1) functionalization of the iodinated isophthalic amine compound or a trimesic acid compound starting material's carboxylic acid groups into acid chlorides as intermediates using traditional methods
2) the compound from step 1) is reacted in dimethyl acetamide at elevated temperature to form non-ionic hydrophilic moiety such as amides moieties of formula (IV). Steps 1 and 2 here correspond to steps a) to c) in the procedure for production of the compound of formula (III) below.

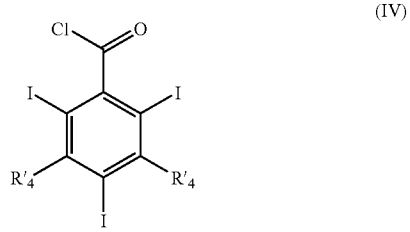

(IV)

wherein $R^{4'}$ denotes a precursor of $R^4$ such as a acid chloride, an alkylated amide group or an acylated amino group 3) the compound of formula (IV) is reacted with an alkyl triamine of formula C [(CX$_2$)$_n$—NHR$^5$]$_3$ under basic conditions and ambient temperature in dimethyl acetamide to produce a triamide derivative (IIa)

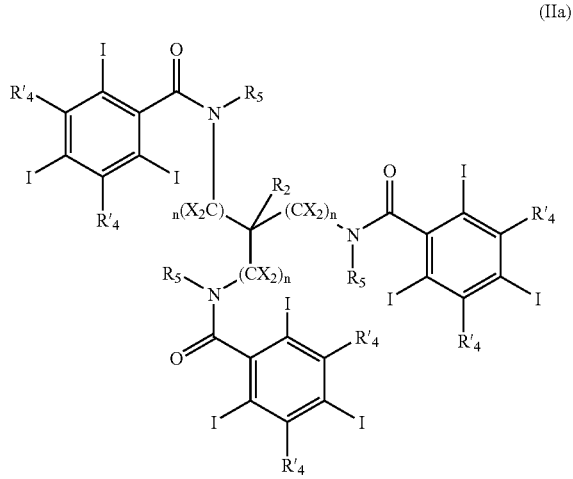

(IIa)

wherein R$^{4'}$ and R$^5$ have the meanings above followed by,
4) if necessary, transformation e.g. by oxidation of R$^{4'}$ group in compound (II) using traditional oxidation methods, such as osmium catalytic reaction followed by,
5) if necessary, hydrolysis of R$^{4'}$ protected groups obtained from step 4) such as esters using traditional deacetylation methods to produce the compound of formula (I).

The final product is then purified by conventional methods such as semi-preparative HPLC.

In step 1) the starting material is converted into the corresponding di-acid chloride or tri-acid chloride by treatment with a solution of thionyl chloride in dichloroethane and pyridine according to the procedure described in E. R Marinelli, *Tetrahedron*, 52, 34, 11177-11214.

The acid chloride is then in step 2) dissolved in dimethyl acetamide together with acetoxy acetyl chloride and/or allyl amide and the solution is heated to about 70° C. After completion of the reaction as determined by analysis of the reaction mixture, the product is isolated by column chromatography. In step 3) the compound (IV) is reacted with a compound of formula C [(CX$_2$)$_n$—NHR$^5$]$_3$ in dimethyl acetamide and triethylamine. After completion of the reaction the desired compound is isolated by aqueous wash and HPLC chromatography. In step 4) the compound of formula (II) is dissolved into a solution of osmium tetroxide at ambient temperature followed by step 5), de-acetylation in methanol and triethylamine to yield after HPLC purification the desire compound of formula (I).

By way of example, the compound of formula (IIIa) is produced according to the following procedure:

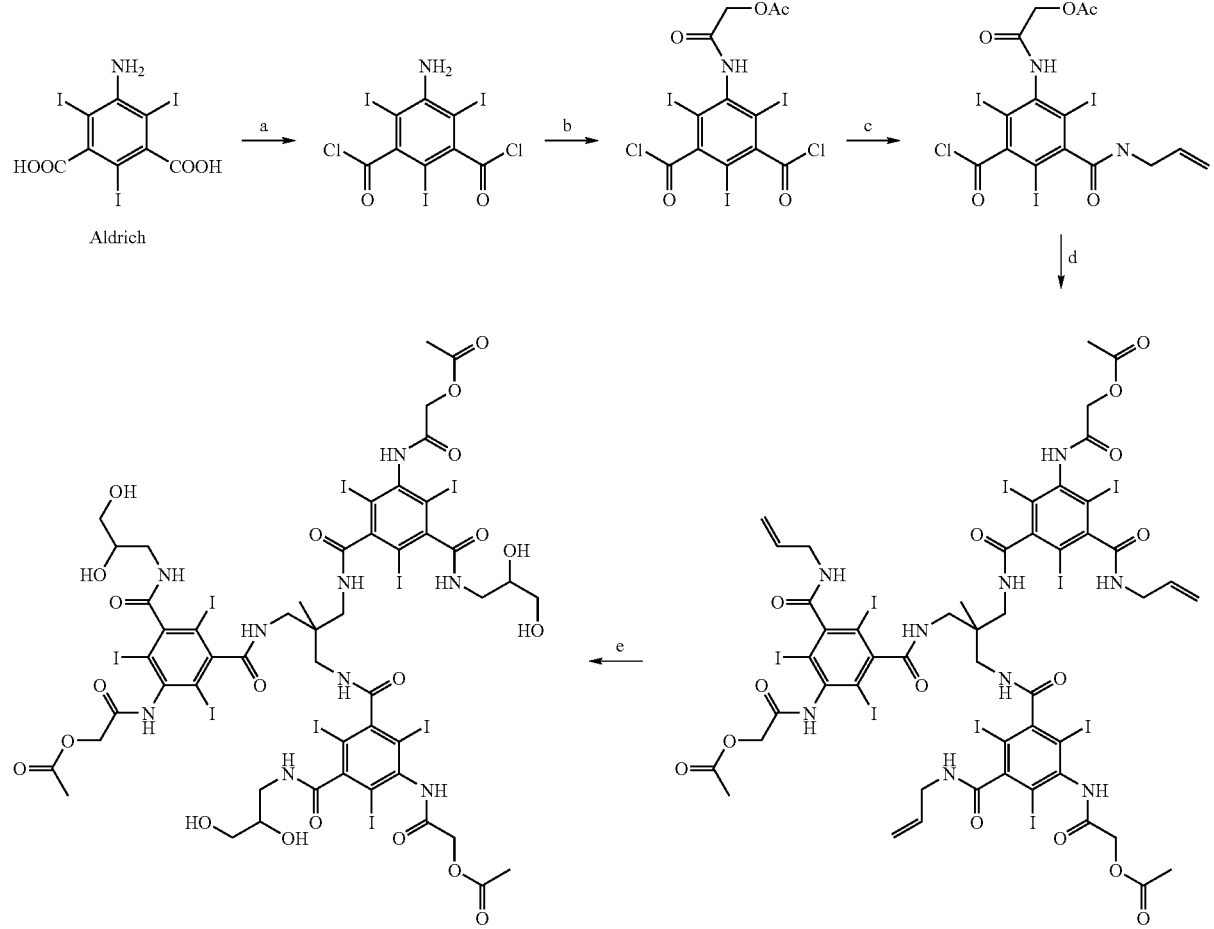

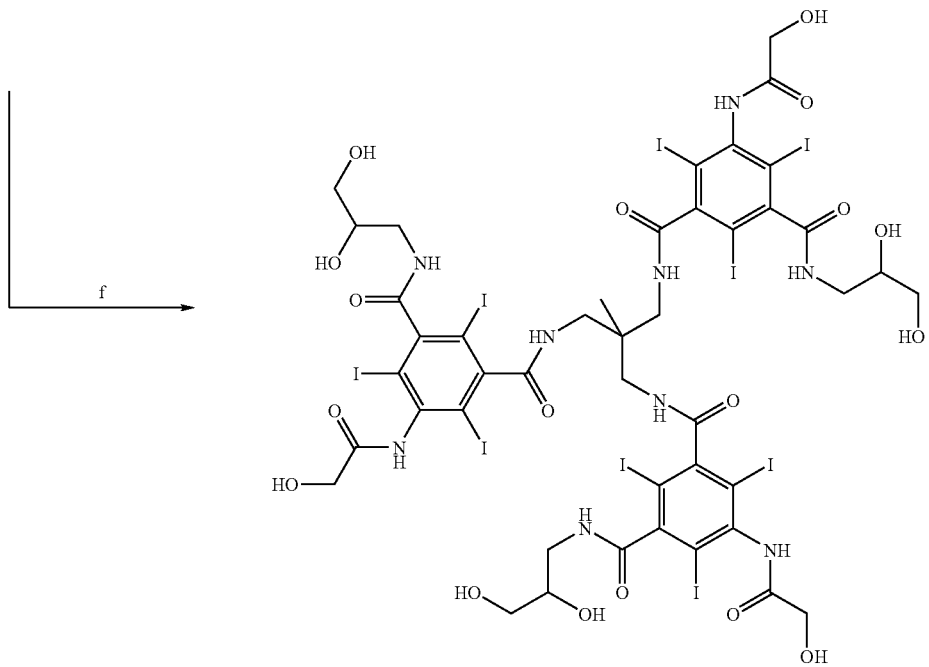

The N-acetylated monoallylamides, specifically the compound N(3-allylcarbamoyl-5-chlorocarbonyl-2,4,6-triiodophenyl)-1-acetoxy acetamide produced in step c) is novel and is useful as an intermediate in the process for the production of compounds of formula (I).

Preparation of Intermediates (A) to (D)

Preparation (A):

Synthesis of 5-Amino-2,4,6-triiodo-isophthaloyl dichloride (1)

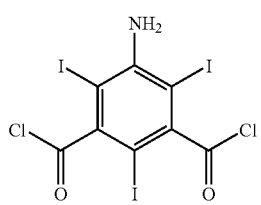

5-Amino-2,4,6-triiodo-isophtalic acid (30 g, 0.054 mol) (commercially available from Aldrich), thionyl chloride (8.2 ml, 0.113 mol) and pyridine (0.2 ml) in 1,2 dichloroethane (20 ml) were heated to 70° C. A portion of thionyl chloride (15.2 ml, 0.21 mol) was added dropwise during 1½ to 2 hrs, and the mixture was heated to 85° C. for 6 hrs. After cooling the reaction mixture to room temperature, it was poured into 300 g of ice-water. The yellow precipitate that formed was filtered off, sucked dry and then washed with water until washings showed a pH of ca 5. The filter cake was then dried in a vacuum oven at 50° C. for 3 hrs. A light yellow powder was obtained 31 g (~quant.) as the desired product.

$^{13}$C NMR (DMSOd$_6$) 66, 78.4, 148.9, 149.2, 169

MS (ES−) found 593.5 [M-H+], expected 593.7

Preparation (B):

Synthesis of 3-(Allyl-methyl-carbamoyl)-5-amino-2,4,6-triiodo-benzoyl chloride (2)

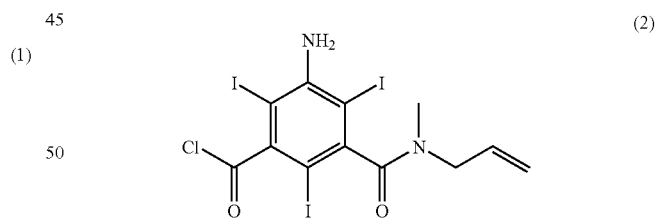

Typically 5-amino-2,4,6,triiodoisophthaloyl dichloride (1) (100 g, 168 mmol) was dissolved in anhydrous THF (500 ml), the N-methyl allylamine (25 ml) was dissolved in 50 ml THF, and added dropwise to the solution over 1 hour. The mixture was heated to 50 deg C. and stirred overnight. The crude mixture was analysed by LCMS and this confirmed that the reaction mixture contained the desired product, 'bis-acid chloride' and 'bis-N-methyl-allylamide'. The reaction was also monitored by TLC (2% MeOH in DCM) on silica gel plates, bis-acid chloride had an R$_f$ of ~0.98, the mono-N-methylallylamide ~0.73 and the bis-N-methylallylamide ~0.25. Once the reaction was deemed complete, the solution was filtered, vacuumed to dryness, then dissolved in 500 ml of ethyl acetate this solution was then loaded onto silica and purified on a 750 g column using ethyl acetate (B) and petrol (A) (10%→100% B over ~10 column volumes). The pure fractions were collected and identified by TLC, the desired fractions were then vacuumed to dryness. The structure was confirmed by $^1$H and $^{13}$C NMR and purity by LCMS.

Preparation (C):

Synthesis of acetic acid
2,3-diacetoxy-3-chlorocarbonyl-propyl ester (3)

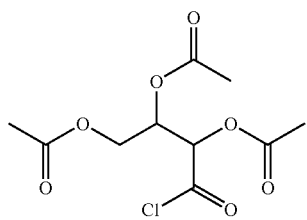

(3)

The 2,3,4-triacetoxy-butyric acid (25 g, 0.095 mol) was stirred in thionyl chloride (15.3 mL) at room temperature with a condenser fitted. The reaction was stirred for 48 hours and then the thionyl chloride was removed under reduced pressure to give an oil, which $^1$H and $^{13}$C NMR (CDCl$_3$) showed to be the desired material (26.1 g, 98%).

Preparation (D):

Synthesis of acetic acid 2,3-diacetoxy-1-[3-(allyl-methyl-carbamoyl)-5-chlorocarbonyl-2,4,6-triiodo-phenylcarbamoyl]-propyl ester (4)

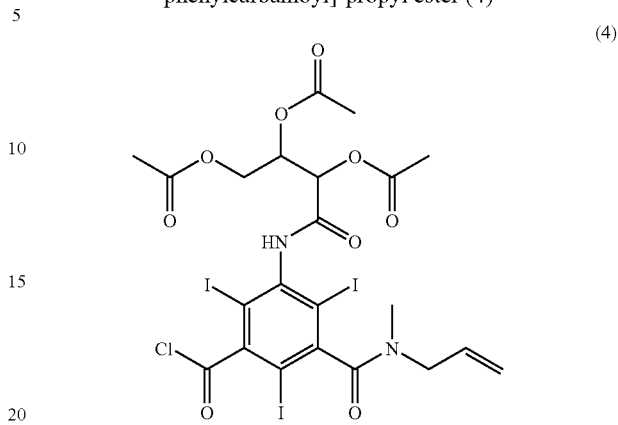

(4)

5-amino-2,4,6-triiodoisophathalic mono-N-methyl allylamide (2) (13.5 g, 0.0214 mol) and threonic acid chloride triacetate (3) (11.1 g, 0.0395 mol) were dissolved in dry dimethylacetamide (60 mL) and stirred for 48 hours at room temperature. The reaction mixture was diluted with ethyl acetate (250 mL) and washed with ice-water/brine (50:50, 5×25 mL). The organics were collected and dried over MgSO$_4$, filtered and evaporated to dryness to give a brown oil. It was purified by column chromatography, eluting with petrol: ethyl acetate (10-100%, 12 column volumes, SiO$_2$, 330 g) to give the desired product as an off white solid (10.1 g, 54%).

The product was confirmed by $^1$H NMR (CDCl$_3$).

EXAMPLE 1

N,N',N''-Tris-{2,4,6-triiodo-3[N-methyl-N-(2,3-dihydroxypropyl)aminocarbonyl]-5-(2,3,4-trihydroxy-butyrylamino)phenyl}-carbamoylethyl methane Following the synthetic scheme depicted below and the procedure described in steps a) to d) the title compound was obtained.

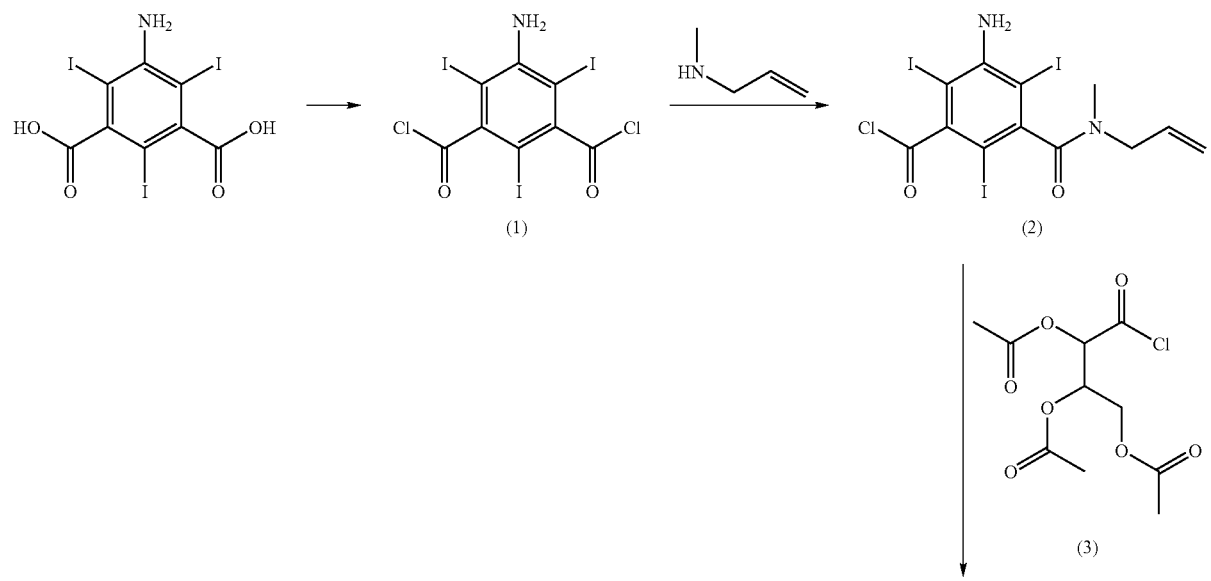

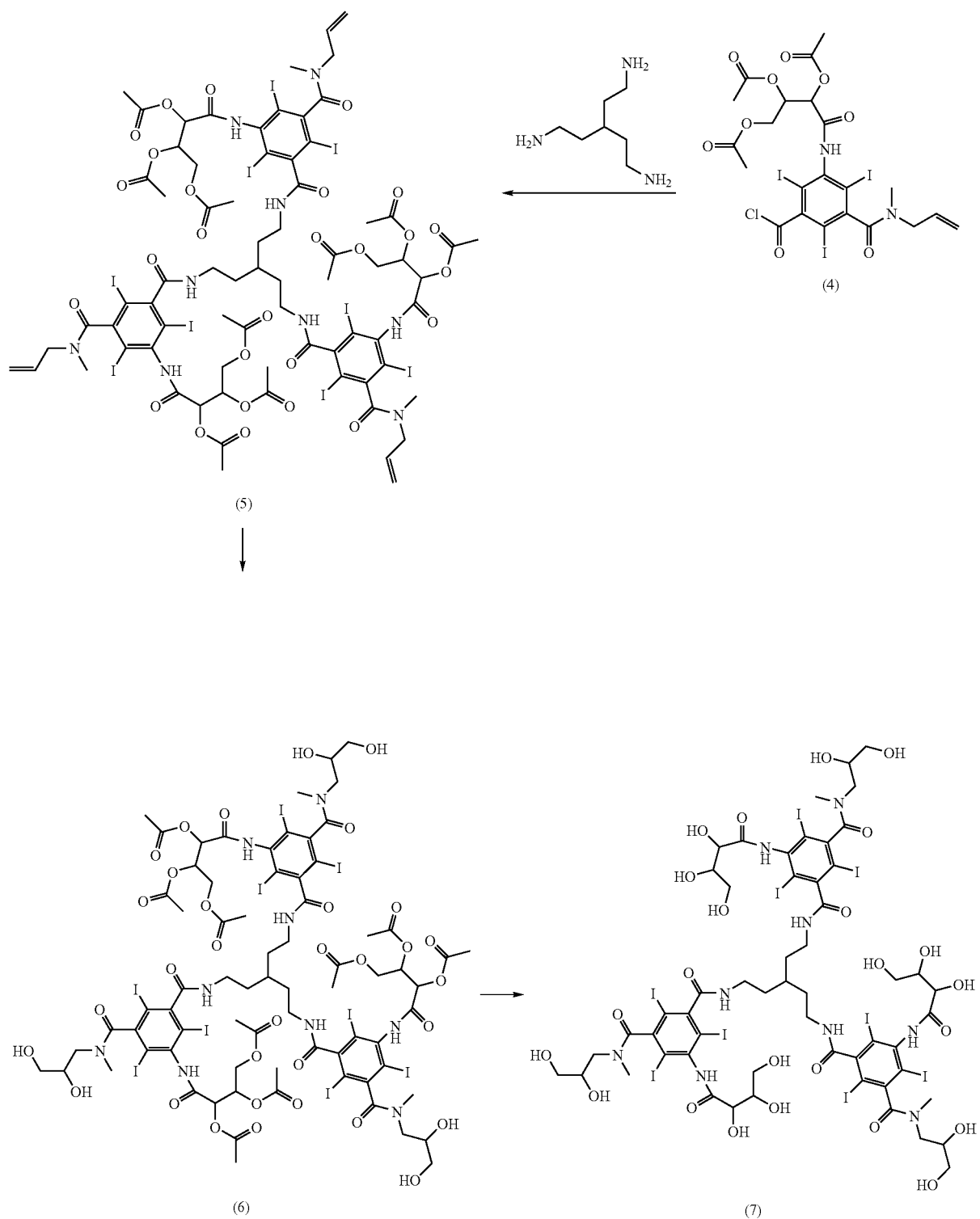

a) 3-(2-Amino-ethyl)-pentane-1,5-diamine

The preparation is described in WO2003006070A2 b) N,N',N''-Tris-{2,4,6-triiodo-3[N-methyl-N-allyl]aminocarbonyl}-5-(2,3,4-triacetoxy-butyrylamino)phenyl)-carbamoylethyl methane (5)

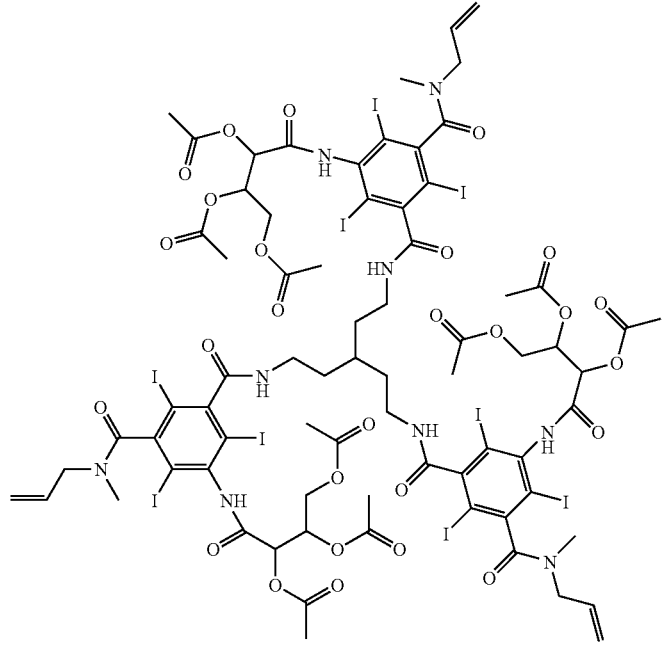

(5)

To a solution of tris(aminoethyl)methane (0.49 g, 3.36 mmol) in dimethylacetamide (20 ml) was added triethylamine (1.99 ml, 14.3 mmol) followed by a solution of acid chloride (4) in dimethylacetamide (20 ml). The mixture was stirred at ambient temperature for 18 hours under nitrogen then heated at 60° C. for 24 h. Excess triethylamine was evaporated at reduced pressure and ethyl acetate (450 ml) was added. The resultant solution was washed with ice-water (4×50 ml), brine, dried (MgSO4) filtered and evaporated to give a brown viscous oil, which was purified by column chromatography on silica gel in 97:3-7:3 ethyl acetate:methanol to give the product as a white solid foam (3.33 g, 37% yield).

MS and $^1$H NMR (CDCl$_3$) were consistent with the structure.

c) N,N',N''-Tris-{2,4,6-triiodo-3[N-methyl-N-(2,3-dihydroxypropyl)aminocarbonyl]-5-(2,3,4-triacetoxy-butyrylamino)phenyl}-carbamoylethyl methane (6)

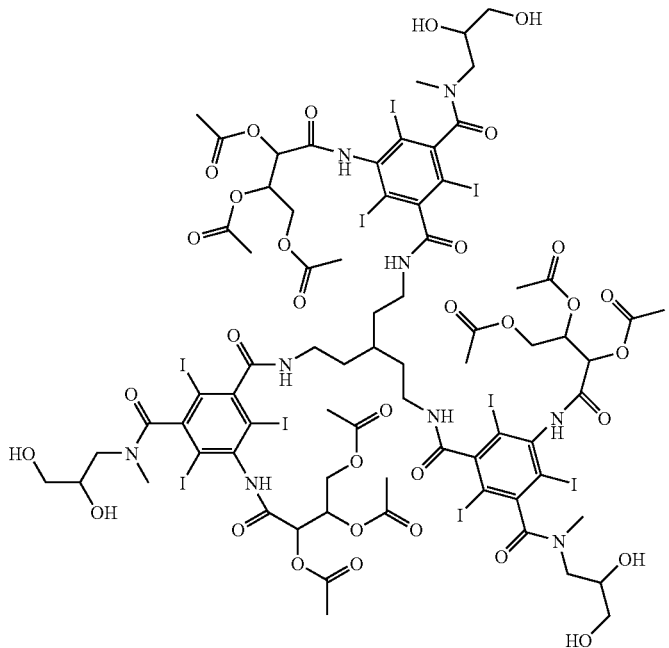

(6)

N,N',N"-Tris-{2,4,6-triiodo-3[N-methyl-N-allyl]aminocarbonyl}-5-(2,3,4-triacetoxy-butyrylamino)phenyl)-carbamoylethyl methane (5) (3.30 g, 1.24 mmol) was dissolved in a mixture of acetone/water (9/1) (30 mL). A solution of osmium catalyst (1.5 mL) (1 g OsO4, 100 ml t-BuOH 100 ml and 10 drops of t-BuOOH) was added followed by addition of N-methylmorpholine oxide (1.75 g). The mixture was stirred over night at ambient temperature, when reaction was shown to be complete by HPLC, the reaction was quenched with a 10 ml solution of sodium hydrogen sulphite (15%) and the mixture was evaporated to dryness. The crude was used without further purification.

d) N,N',N"-Tris-{2,4,6-triiodo-3[N-methyl-N-(2,3-dihydroxypropyl)aminocarbonyl]-5-(2,3,4-trihydroxy-butyrylamino)phenyl}-carbamoylethyl methane (7)

The crude N,N',N"-Tris-{2,4,6-triiodo-3[N-methyl-N-(2,3-dihydroxypropyl)aminocarbonyl]-5-(2,3,4-triacetoxy-butyrylamino)phenyl}-carbamoylethyl methane (6) was dissolved in 1:1 methanol:water and concentrated ammonia solution (32%, 2 ml) was added. After stirring for 24 hours, HPLC showed all starting material was consumed and the solvents were evaporated. The crude solid was recrystallized from hot ethanol to yield an off-white solid (2 g) from which the product was isolated by preparative HPLC. The required fractions were freeze-dried to yield a white solid (450 mg) which was found to be the desired compound.

MS (ES+) m/2: 1193[M+H].

EXAMPLE 2

N,N',N"-Tris-{2,4,6-triiodo-3[N-methyl-N-(2,3-dihydroxypropyl)aminocarbonyl]-5-(2,3,4-trihydroxy-butyrylamino)phenyl}-carbamoylpropyl methane Following the synthetic scheme depicted below and the procedure described in steps a) to d) the title compound was obtained.

(7)

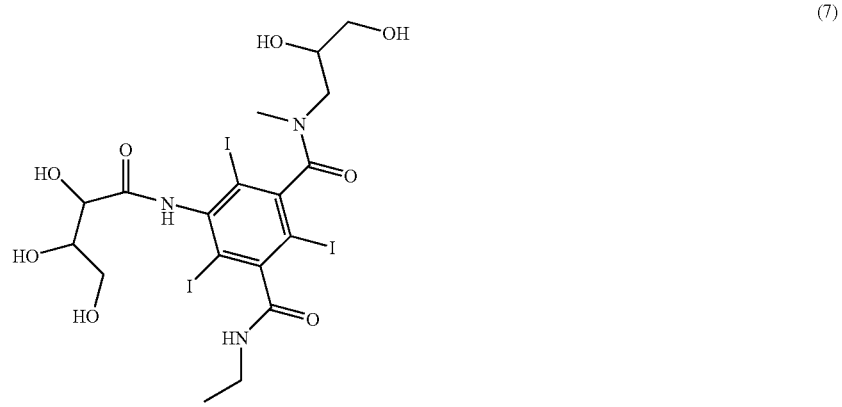

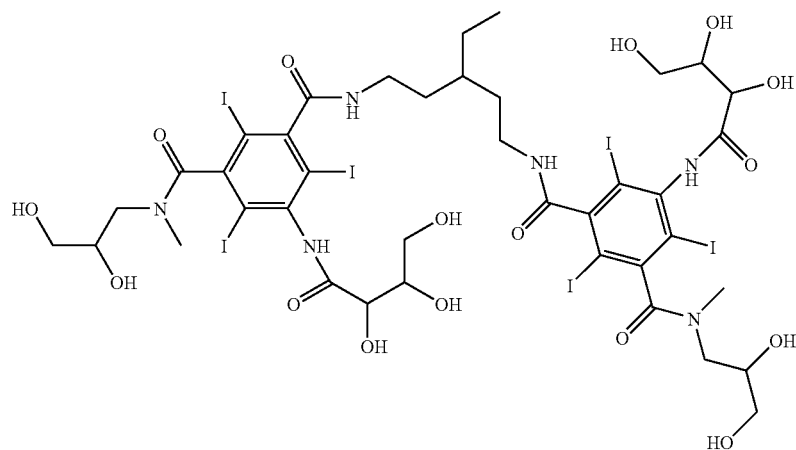

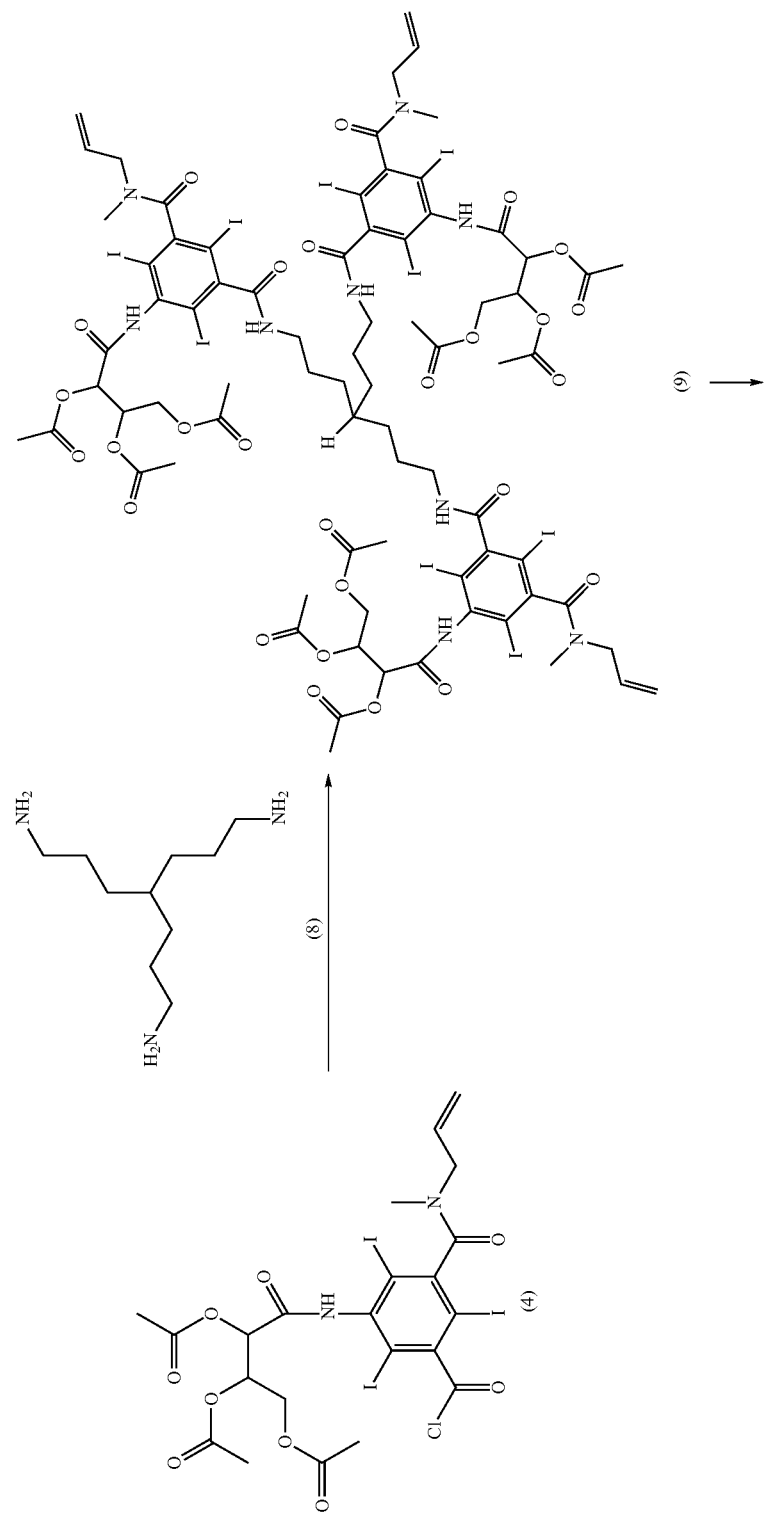

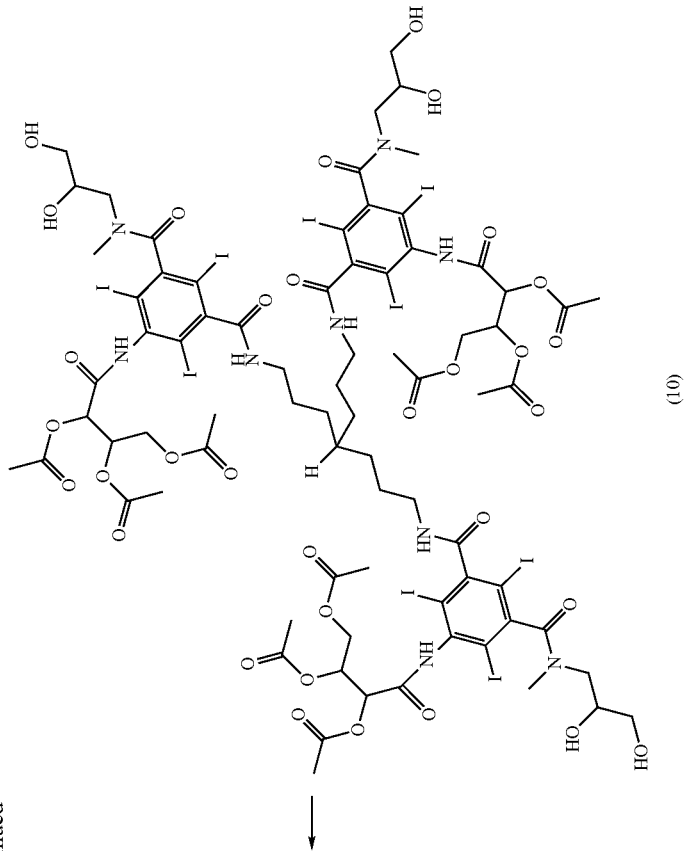
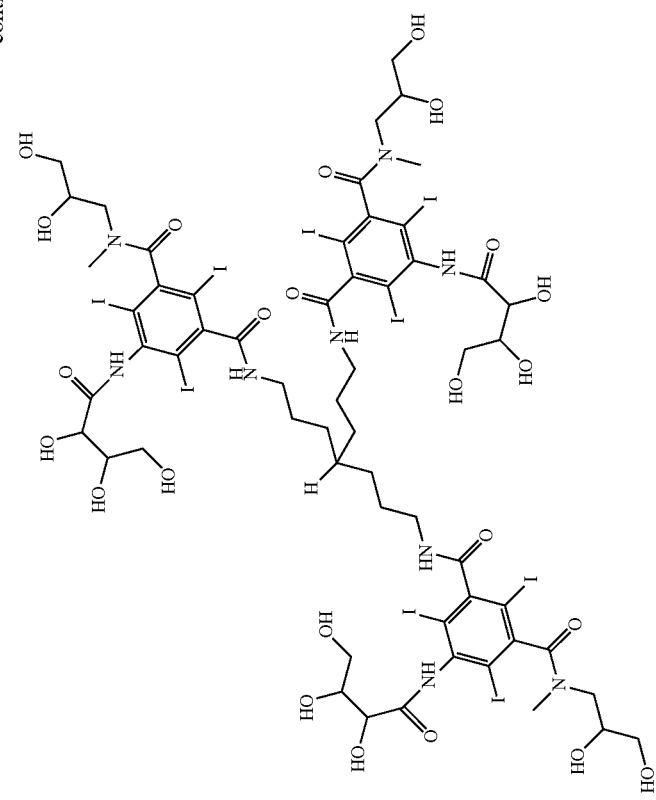

a) 4-(3-Amino-propyl)-heptane-1,7-diamine (8)

was preparation as described in Hahn & Tamm, Angew. Chem., Int. Ed. Engl., 1992, 31(9), 1212-14.

b) N,N',N''-Tris-{2,4,6-triiodo-3[N-methyl-N-allyl] aminocarbonyl}-5-(2,3,4-triacetoxy-butyrylamino) phenyl)-carbamoylpropyl methane (9)

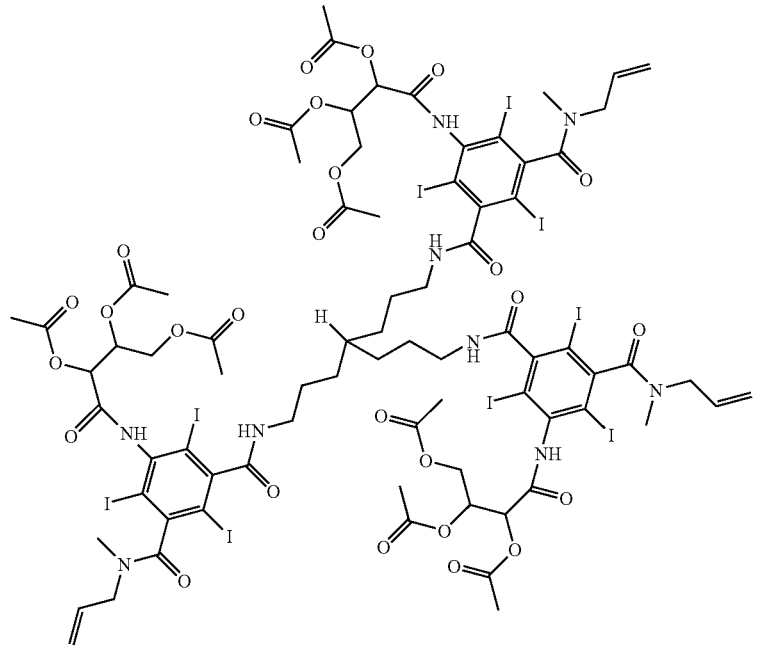

(9)

To a solution of 4-(3-Amino-propyl)-heptane-1,7-diamine (0.63 g, 3.36 mmol) in dimethylacetamide (20 ml) is added triethylamine (1.99 ml, 14.3 mmol) followed by a solution of acid chloride (4) in dimethylacetamide (20 ml). The mixture is stirred at ambient temperature for 18 hours under nitrogen then heated at 60° C. for 24 h. Excess triethylamine is evaporated at reduced pressure and ethyl acetate (450 ml) is added. The resultant solution is washed with ice-water (4×50 ml), brine, dried (MgSO4) filtered and evaporated to give a brown viscous oil, which is purified by column chromatography on silica gel in 97:3-7:3 ethyl acetate:methanol to give the product as a white solid foam.

MS and $^1$H NMR (CDCl$_3$) are consistent with the structure.

c) N,N',N''-Tris-{2,4,6-triiodo-3[N-methyl-N-(2,3-dihydroxypropyl)aminocarbonyl]-5-(2,3,4-triacetoxy-butyrylamino)phenyl}-carbamoylpropyl methane (10)

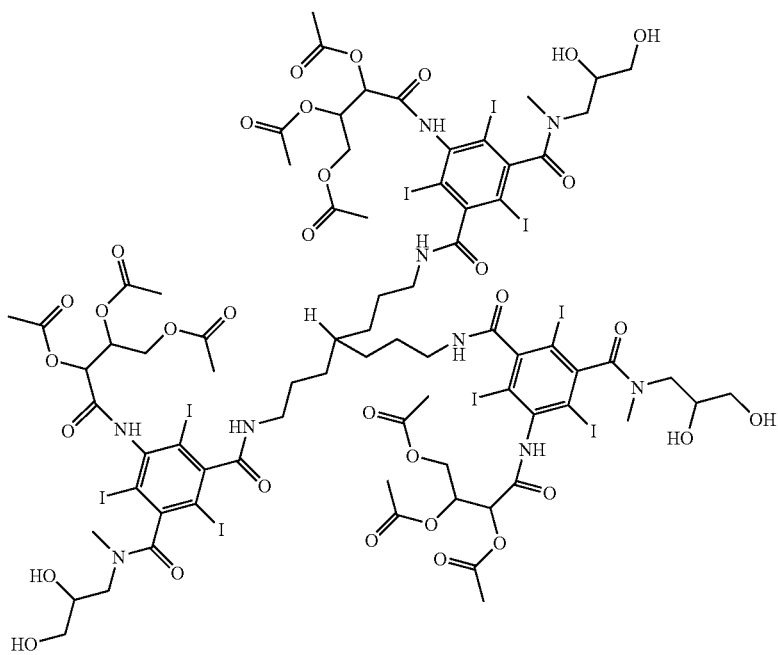

(10)

N,N',N''-Tris-{2,4,6-triiodo-3[N-methyl-N-allyl]aminocarbonyl}-5-(2,3,4-triacetoxy-butyrylamino)phenyl)-carbamoylpropyl methane (9) (3.48 g, 1.24 mmol) is dissolved in a mixture of acetone/water (9/1) (30 mL). A solution of osmium catalyst (1.5 mL) (1 g OsO4, 100 ml t-BuOH 100 ml and 10 drops of t-BuOOH) is added followed by addition of N-methylmorpholine oxide (1.75 g). The mixture is stirred over night at ambient temperature, when reaction is shown to be complete by HPLC, the reaction is quenched with a 10 ml solution of sodium hydrogen sulphite (15%) and the mixture is evaporated to dryness. The crude is used without further purification.

d) N,N',N''-Tris-{2,4,6-triiodo-3[N-methyl-N-(2,3-dihydroxypropyl)aminocarbonyl]-5-(2,3,4-trihydroxy-butyrylamino)phenyl}-carbamoylpropyl methane (11)

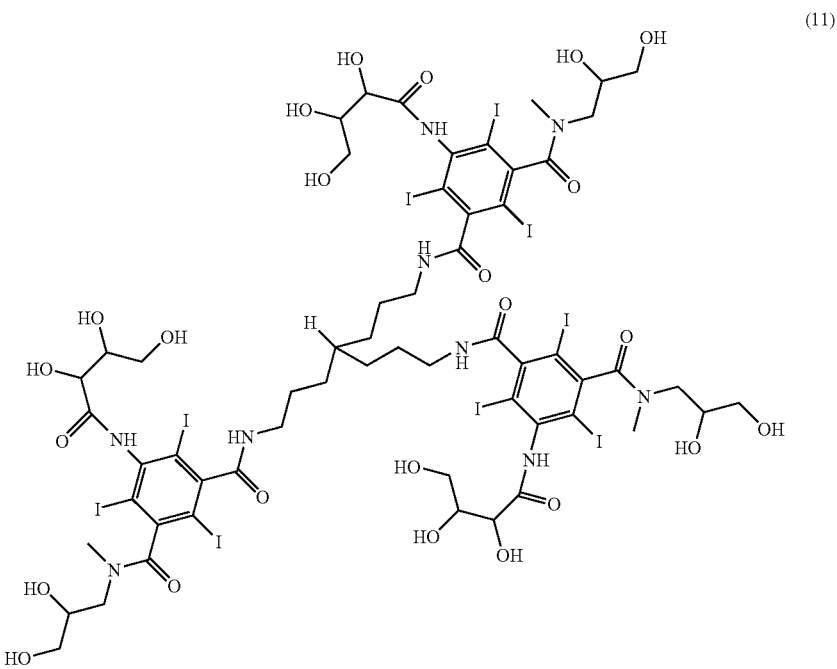

(11)

The crude N,N',N''-Tris-{2,4,6-triiodo-3[N-methyl-N-(2,3-dihydroxypropyl)aminocarbonyl]-5-(2,3,4-triacetoxy-butyrylamino)phenyl}-carbamoylpropyl methane (10) is dissolved in 1:1 methanol:water and concentrated ammonia solution (32%, 2 ml) is added. After stirring for 24 hours, HPLC shows all starting material is consumed and the solvents are evaporated. The crude solid is recrystallized from hot ethanol to yield an off-white solid (2 g) from which the product is isolated by preparative HPLC. The required fractions are freeze-dried to yield a white solid.

EXAMPLE 3

N,N',N''-Tris-{2,4,6-triiodo-3[N-methyl-N-(2,3-dihydroxypropyl)aminocarbonyl]-5-(2,3-dihydroxybutyrylamino)phenyl}-carbamoylethyl methane Following the synthetic scheme depicted below and the procedure described in steps a) to g) the title compound was obtained.

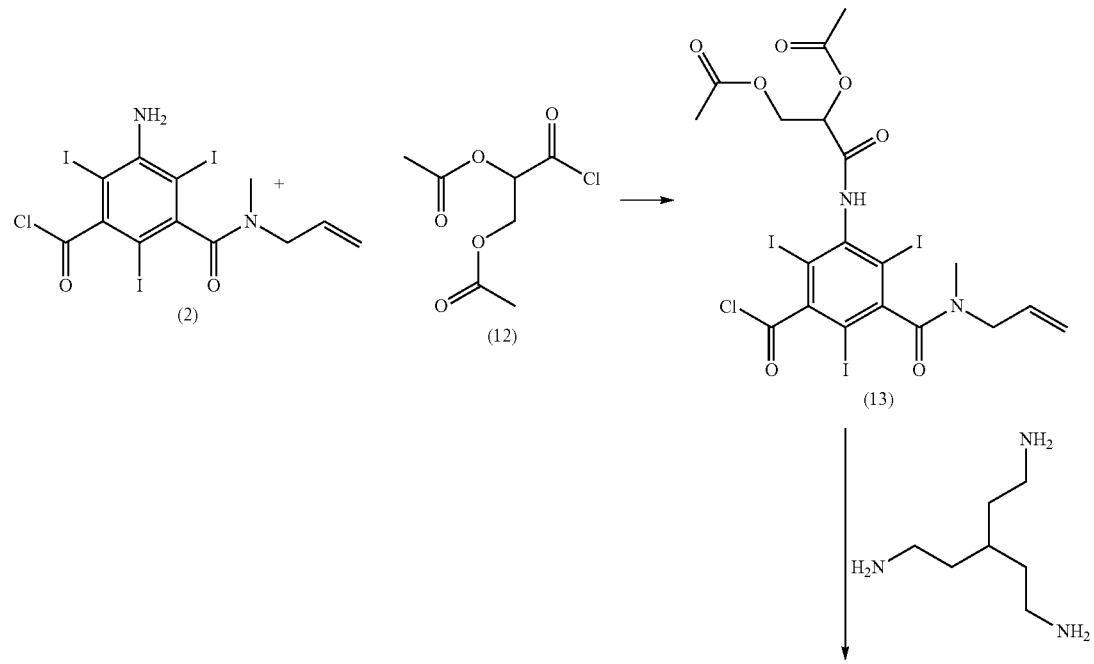
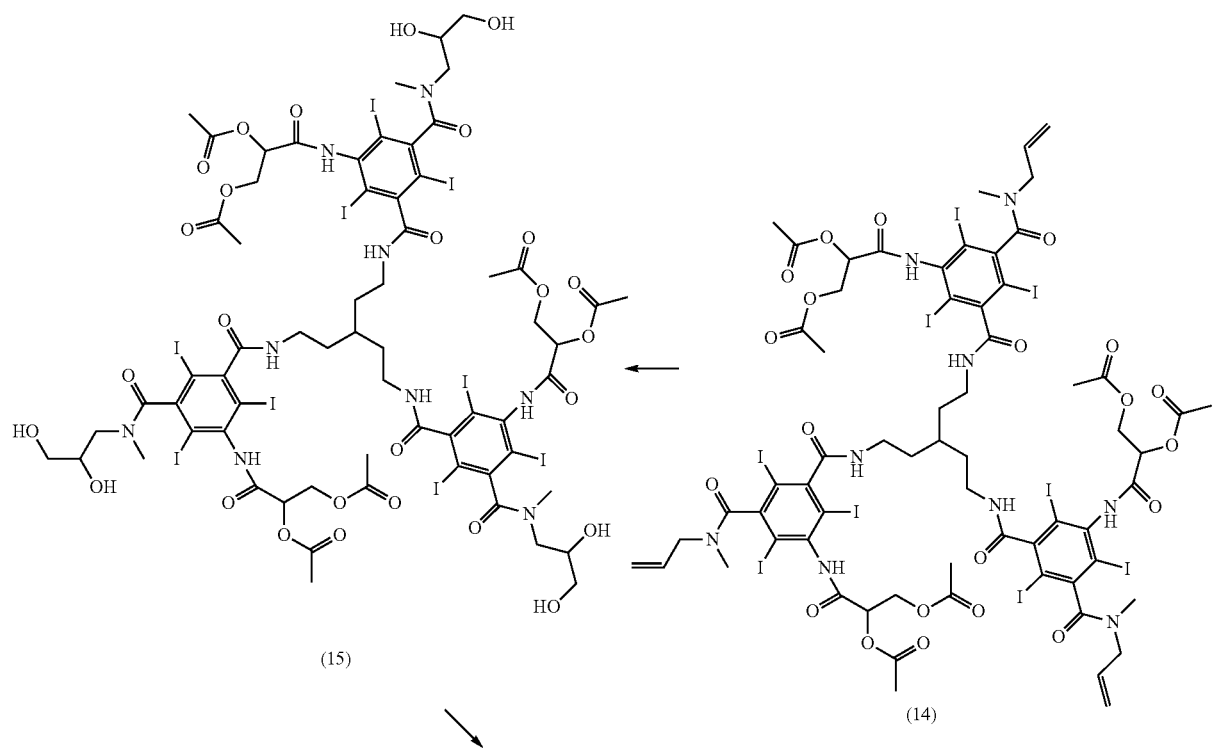

-continued

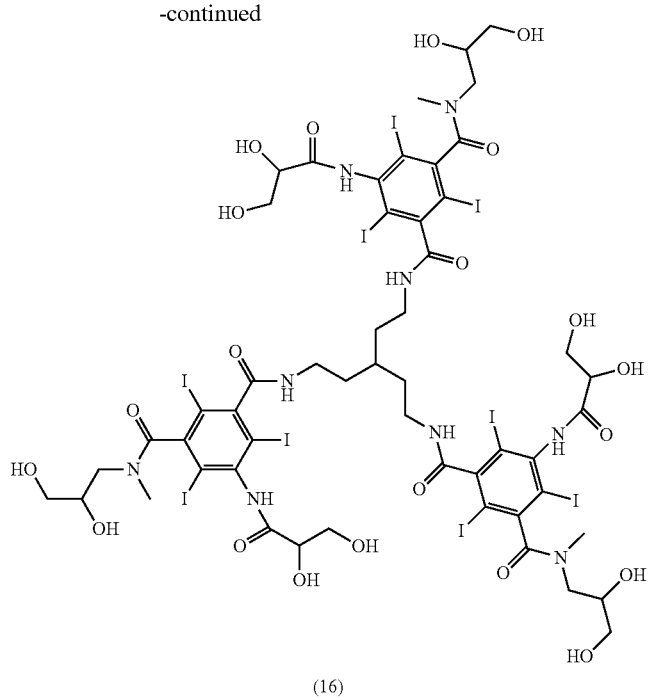

(16)

a) Synthesis of lithium 2,3-dihydroxypropanoate

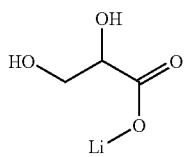

D,L-Serine (115.5 g, 1.10 mole) was added to a mixture of conc. sulfuric acid (75 g) in water (1.25 L) and the mixture was cooled to ca 5° C. Sodium nitrite (68.3 g, 0.99 mole) dissolved in water (500 ml) was added slowly during 3 h while temperature was kept at 5°-10° C. Then sulfuric acid (60 g) dissolved in water (200 ml) and cooled to ca 5° C. in a ice/water mixture, was added. A new portion of sodium nitrite (68.3 g, 0.99 mole) dissolved in water (500 ml) was added slowly during 2 h, while temperature was kept at 5°-10° C. The mixture was stirred at ambient temperature over night and then concentrated to a volume of ca 700 ml. Lithium hydroxide (22.7 g, 0.95 mole), dissolved in water (100 ml) was added. The mixture was now poured into a stirred mixture of methanol (1 L) and acetone (0.3 L). The precipitate formed was filtered off and washed with methanol/acetone (1/0.3 100 ml). The combined filtrates were now evaporated to a small volume (ca. 300 ml) and pH was adjusted to 7 by addition of a 5M solution of lithium hydroxide (ca. 200 ml). The mixture was evaporated to dryness and abs. ethanol (600 ml) was added, the product dissolved by heating and the mixture evaporated to dryness. The residue was then co evaporated twice with toluene (2×300 ml), and pumped in vacuo. There was of a gum like product 130 g. Identity was checked by $^1$H NMR in $D_2O$.

b) Synthesis of 2,3-diacetoxypropanoic acid

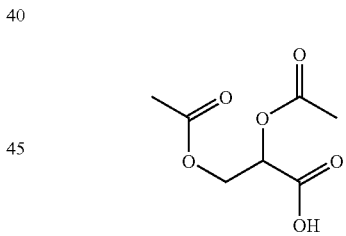

Acetyl chloride (500 ml) was added dropwise without stirring to the gummy like mass of lithium 2,3-dihyroxypropanoate (13) (171 g, 1.51 mole). The gummy like mass dissolved slowly and the mixture was left for 24 h at ambient temperature. Then the mixture was stirred and heated to reflux for 6 h. After cooling the mixture was diluted with ethyl acetate (700 ml) and filtered through a tight glass filter (por. G4). The filtrate was evaporated to a oil, which was dissolved in ethyl acetate (750 ml) and washed with water (2×70 ml, pH=2). After drying over magnesium sulfate and treatment with activated charcoal (1.5 g) the mixture was filtered. The filtrate was evaporated to a light orange coloured oil. Yield (crude) 218 g (75%).

Purity checked by $^1$HNMR in $CDCl_3$.

c) Synthesis of 2,3-diacetoxypropanoyl chloride (12)

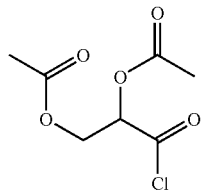

(12)

Thionyl chloride (62 ml, 0.86 mole) was added dropwise to 2,3-diacetoxypropanoic acid (14) in a flask to which a drop of N,N-dimethylformamide had been added. The mixture was then stirred at ambient temperature over night and then evaporated to a syrup at a temperature ≦40° C. The syrup was taken up in diethyl ether (60 ml) and activated charcoal (0.3 g) added. The mixture was then filtered through a tight glass filter and evaporated in vacuo (10 torr). The oily residue was distilled in a Kugelrohr apparatus to give 24.6 g (68%). Identity and purity checked by $^1$HNMR in CDCl$_3$.

d) Synthesis of acetic acid 2-acetoxy-2-[3-(allyl-methyl-carbamoyl)-5-chlorocarbonyl-2,4,6-triiodo-phenylcarbamoyl]-ethyl ester (13)

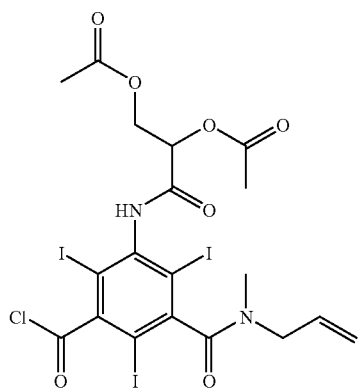

(13)

3-(Allyl-methyl-carbamoyl)-5-amino-2,4,6-triiodo-benzoyl chloride (2) (0.19 mol, 120 g) was dissolved in dry N,N-dimethyl acetamide (DMA) (480 ml) and the acid chloride (10) (0.38 ml, 79 g) was added dropwise. The clear yellow red reaction mixture was stirred at overnight at ambient temperature, with nitrogen bubbling through the reaction mixture. The reaction was monitored by TLC on silica gel plates eluting with ethyl acetate: petrol (1:1). After 19 hours the reaction was stopped and the brown solution was diluted with ethyl acetate (~2.4 L) and washed with ice water/brine (50:50, 480 ml×5). The filtrate was washed again with ethyl acetate. 500 ml of filtrate washed twice with 250 ml of ethyl acetate. The brown solution was poured into a 6 L separating funnel and treated with 200 ml of cold water/brine (1:1) solution. The organics were dried over MgSO$_4$, filtered and concentrated. The brown oil obtained was dried under high vacuum over night and analysed via LCMS. One major peak was observed with a mass of 803 (M+H$^+$) and a purity of 86%. $^1$H NMR was carried out (CDCl$_3$). The NMR spectrum showed residual ethyl acetate. The brown oil was left under high vacuum at 40° C. for 1 hour and then left over night under high vacuum at ambient temperature. The mixture was dissolved in ethyl acetate and supported onto silica gel and purified by silica gel chromatography eluting with ethyl acetate/petrol. The off white solid was dried over night under high vacuum at room temperature and this gave a yield of 56%. LCMS was carried out Luna C18 250×4.6 10 u. Purity 95%, $^1$H NMR (CDCl$_3$) confirmed structure of the desired compound.

e) N,N',N''-Tris-{2,4,6-triiodo-3[N-methyl-N-allyl]aminocarbonyl}-5-(2,3-diacetoxy-propylamino)phenyl)-carbamoylethyl methane (14)

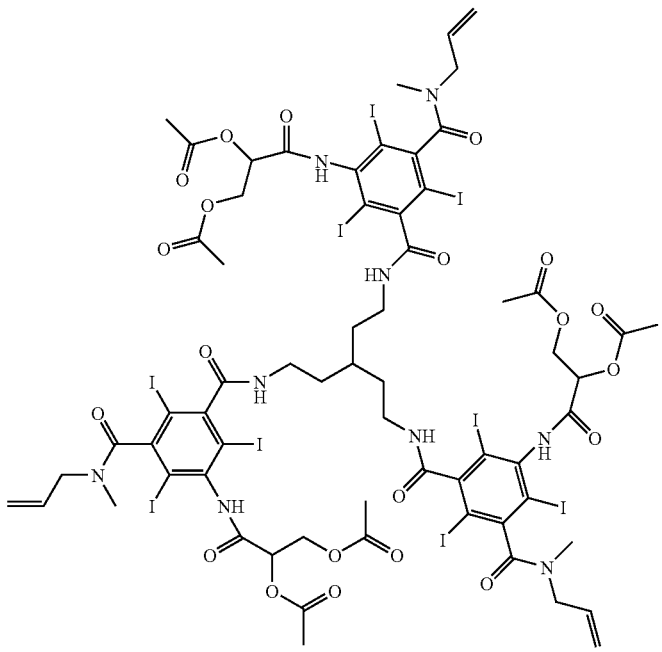

(14)

To a solution of 3-(2-Amino-ethyl)-pentane-1,5-diamine (0.26 g, 1.77 mmol) in dimethylacetamide (5 ml) was added triethylamine (0.99 ml, 7.08 mmol) followed by a solution of acid chloride (13) (5.68 g, 7.08 mmol) in dimethylacetamide (5 ml). The mixture was stirred at ambient temperature for 18 hours under nitrogen then heated at 40° C. for 4 h. Excess triethylamine was evaporated at reduced pressure and ethyl acetate (100 ml) was added. The resultant solution was washed with ice-water (3×50 ml), brine, dried (MgSO4) filtered and evaporated to give a crude product, which was purified by column chromatography on silica gel in 97:3-17:3 ethyl acetate:methanol to give the product as a white solid foam (3.8 g, 88% yield).

MS (ES+) m/2: 1222.20 [M+H]

f) N,N',N''-Tris-{2,4,6-triiodo-3[N-methyl-N-(2,3-dihydroxypropyl)aminocarbonyl]-5-(2,3-diacetoxy-propylamino)phenyl}-carbamoylethyl methane (15)

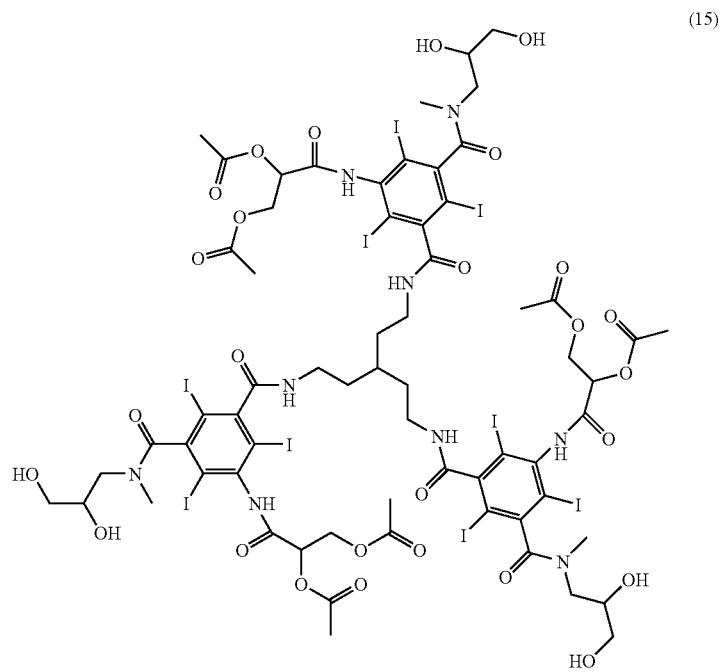

N,N',N''-Tris-{2,4,6-triiodo-3[N-methyl-N-allyl]aminocarbonyl}-5-(2,3-diacetoxy-propylamino)phenyl)-carbamoylethyl methane (14) (3.80 g, 1.5 mmol) was dissolved in a mixture of acetone/water (25/9) (68 mL). A solution of osmium catalyst (2 mL) (1 g OsO4, 100 ml t-BuOH 100 ml and 10 drops of t-BuOOH) was added followed by addition of N-methylmorpholine oxide (730 mg, 6 mmol). The mixture was stirred over night at ambient temperature, when reaction was shown to be complete by HPLC, the reaction was quenched with a 10 ml solution of sodium hydrogen sulphite (15%) and the mixture was evaporated to dryness. The crude was used without further purification.

MS (ES+) m/2: 1272.93 [M+H]

g) N,N',N''-Tris-{2,4,6-triiodo-3[N-methyl-N-(2,3-dihydroxypropyl)aminocarbonyl]-5-(2,3-dihydroxybutyrylamino)phenyl}-carbamoylethyl methane (16)

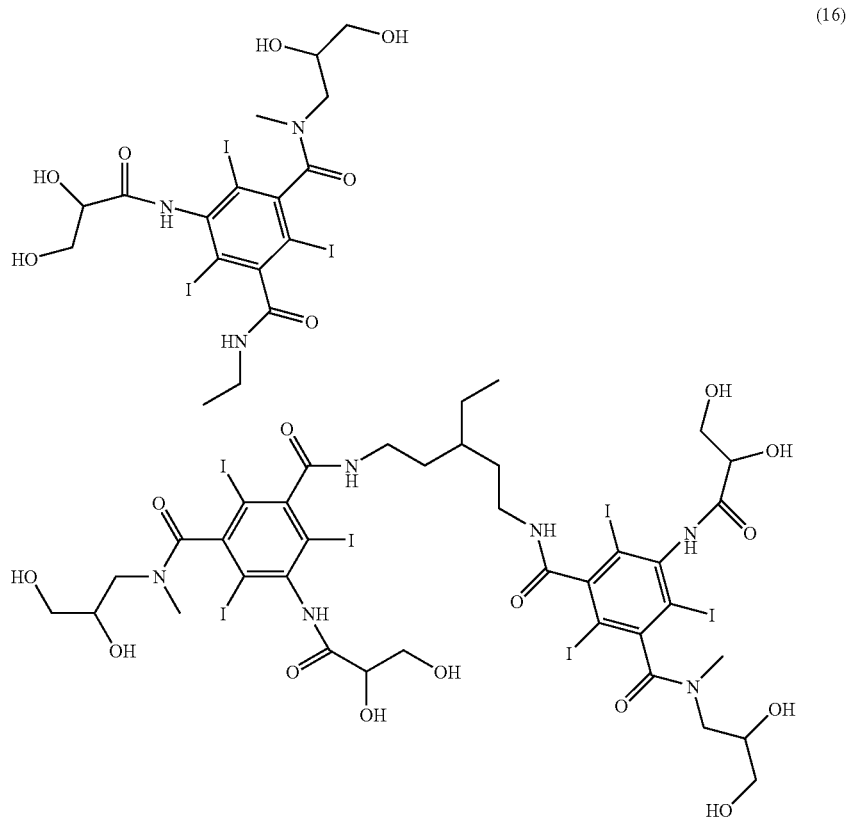

(16)

The crude N,N',N''-Tris-{2,4,6-triiodo-3[N-methyl-N-(2,3-dihydroxypropyl)aminocarbonyl]-5-(2,3-diacetoxy-propylamino)phenyl}-carbamoylethyl methane (15) was dissolved in 1:2 methanol:water (60 ml) and concentrated ammonia solution (32%, 20 ml) was added. After stirring for 24 hours, HPLC showed all starting material was consumed and the solvents were evaporated. The product was isolated by preparative HPLC. The required fractions were freeze-dried to yield a white solid (1.0 g) which was found to be the desired compound.

EXAMPLE 4

Preparation of tris(N-(5-(N''-2,3-diacetoxypropanoylamino)-3-N'-2,3-dihydroxy-N'-methylaminocarbonyl-2,4,6-triiodobenzoyl)amino)methane Following the procedure described in steps a) to e) the title compound was obtained.

a) Preparation of 2-aminomethyl-1,3-diaminopropane

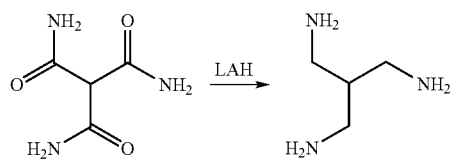

An ice-cooled solution of the triamide (2 g, 13 mmol) in tetrahydrofuran (50 ml) under nitrogen is treated with lithium aluminium hydride (13 ml of a 1M solution in THF, 13 mmol). The mixture is stirred at room temperature for 24 hours and then quenched by addition of water (20 ml). The solvents are removed in vacuo and the residue partitioned between 2M sodium hydroxide and ethyl acetate. The organics are separated, dried over magnesium sulphate, filtered and evaporated to give the desired product.

b) Synthesis of 3-(N-allyl-N-methylaminocarbonyl)-5-(N'-2,3-diacetoxypropanoyl)amino-2,4,6-triiodo-benzoylchloride

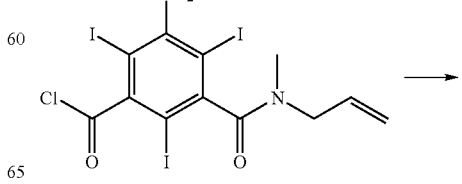

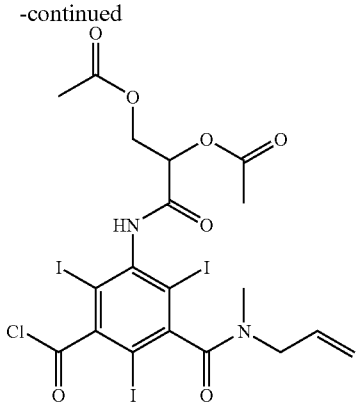

3-(N-Allyl-N-methylaminocarbonyl)-5-amino-2,4,6-triiodo-benzoyl chloride (120 g, 0.19 mol) was dissolved in dry N,N-dimethylacetamide (DMA) (480 ml) and 2,3-triacetoxypropanoyl chloride (79 g, 0.38 mol) was added dropwise. The reaction mixture was stirred at overnight at ambient temperature, with nitrogen bubbling through the reaction mixture. The solution was diluted with ethyl acetate (~2.4 l) and washed with ice water/brine (50:50, 480 ml×5). The organics were dried over magnesium sulfate, filtered and concentrated. The oil was purified by silica gel chromatography eluting with ethyl acetate/petrol to give the desired product as an off-white solid (85 g, 56%).

c) Preparation of tris(N-(3-N'-allyl-N'-methylaminocarbonyl-5-(N''-2,3-diacetoxypropanoylamino)-2,4,6-triiodobenzoyl)amino)methane

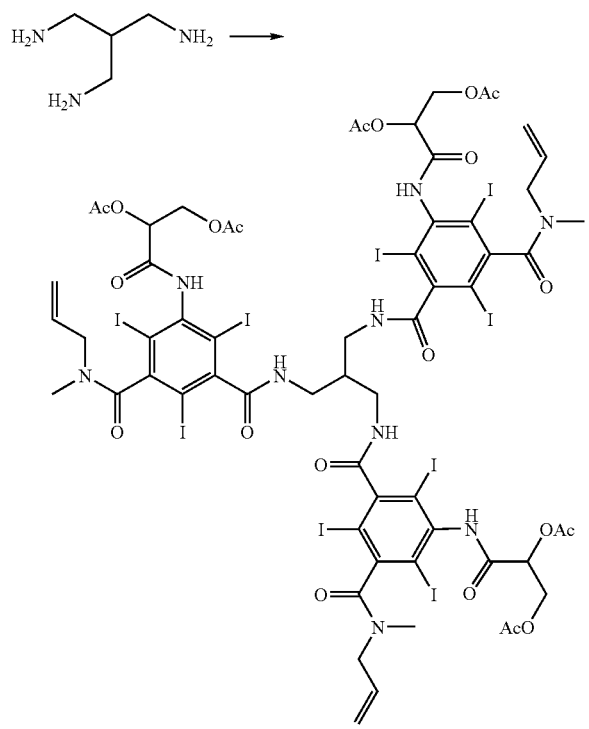

3-(N-allyl-N-methylaminocarbonyl)-5-(N'-2,3-diacetoxypropanoyl)amino-2,4,6-triiodobenzoylchloride (1.6 g, 2 mmol) in anhydrous N,N-dimethylacetamide (20 ml) is treated with the triamine (67 mg, 0.67 mmol) and triethylamine (0.2 g, 2 mmol) at ambient temperature under nitrogen. Once the reaction is complete, the mixture is treated with water (100 ml) and extracted with ethyl acetate (3×100 ml). The combined extracts are dried over magnesium sulfate, filtered and evaporated and the resulting material is purified by flash chromatography in ethyl acetate/petrol.

d) Preparation of tris(N-(5-(N''-2,3-diacetoxypropanoylamino)-3-N'-2,3-dihydroxy-N'-methylaminocarbonyl-2,4,6-triiodobenzoyl)amino)methane

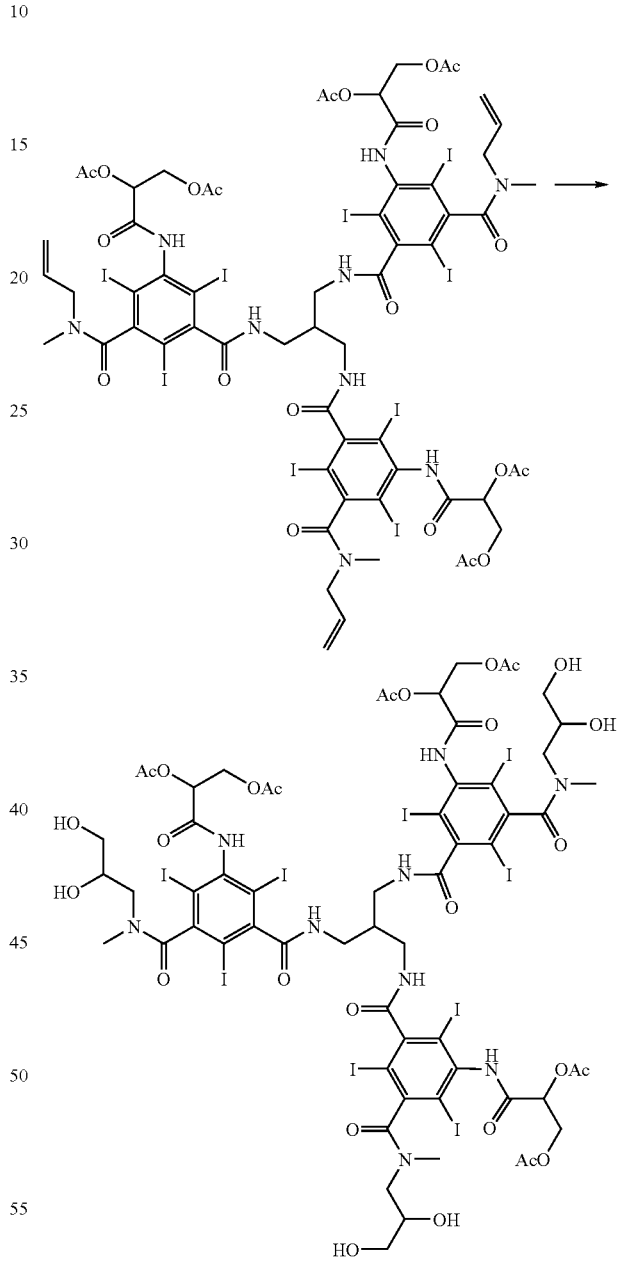

The trimer (1.2 g, 0.5 mmol) dissolved in the minimum of acetone/water (9:1) is next treated with osmium catalyst (1 ml of a solution of $OsO_4$ (1 g) in tert-butanol (100 ml) and tert-butyl hydroperoxide (10 drops)) and N-methylmorpholine N-oxide (1.2 g, 10 mmol). The reaction is worked up by quenching the reaction with a 15% aqueous solution of sodium hydrogensulfite (15 ml) the mixture is evaporated to dryness. The crude material is used in the next step without further purification.

e) Preparation of tris(N-(5-(N''-2,3-diacetoxypropanoylamino)-3-N'-2,3-dihydroxy-N'-methylaminocarbonyl-2,4,6-triiodobenzoyl)amino)methane
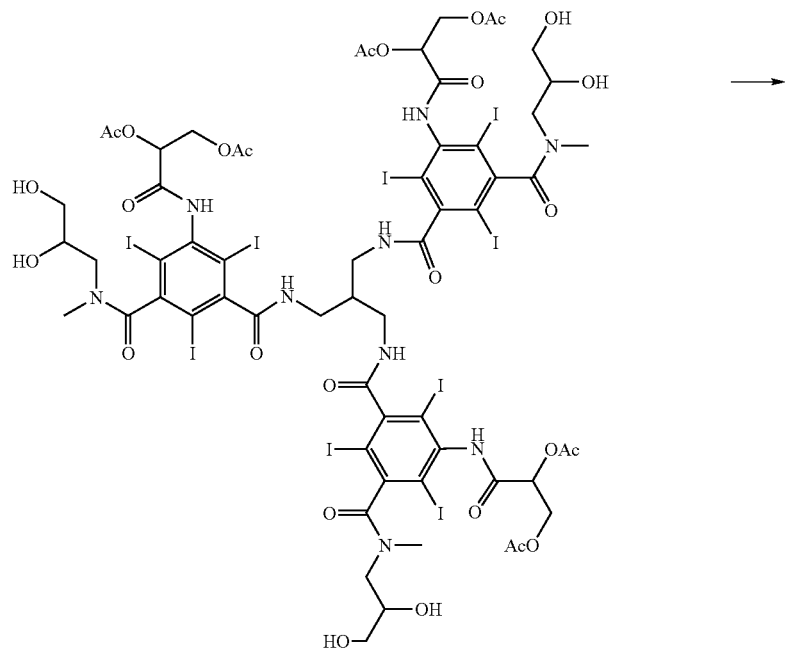
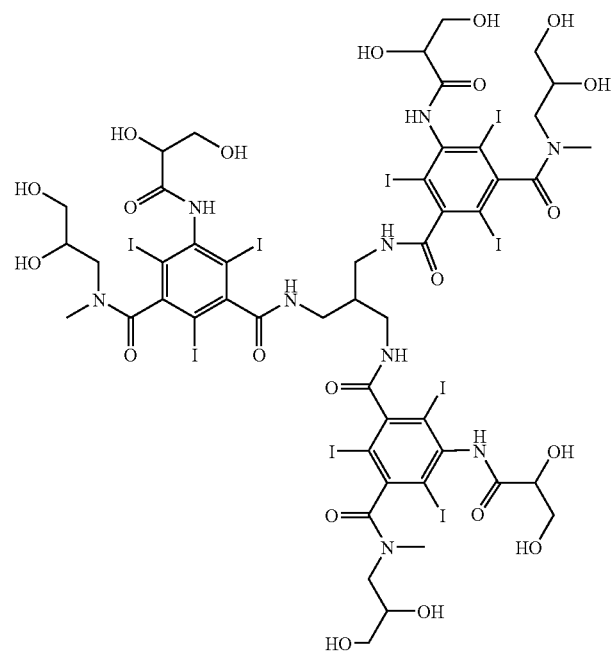

The hexaaacetate (1.2 g, 0.5 mmol) is dissolved in methanol (20 ml) and treated with 0.880 ammonia (1 ml). The mixture is stirred for 2 hours. The solvent is removed in vacuo and the resulting solid is purified by HPLC using acetonitrile/water.

EXAMPLE 5

N,N',N''-Tris-[(3(N-methyl-2,3-dihydroxypropylcarbamoyl)-2,4,6-triiodo-(2,3-dihydroxy-propionylamino) phenyl) carbamoyl methyl ethane Following the synthetic scheme depicted below and the procedure described in steps a] to p) the title compound was obtained.

a) Synthesis of 3-Amino-5-diallylcarbamoyl-2,4,6-triiodo-benzoyl chloride (9)

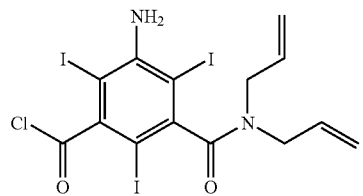

(9)

The Bis acid chloride (6) (50 g, 84 mmol) was dissolved in anhydrous THF (200 ml), the N,N'-di-allylamine (21 ml, 168 mmol) was dissolved in 50 ml THF, and added dropwise to the solution over 1 hour. The mixture was heated to 50 deg C. and stirred overnight. The crude mixture was analysed by LCMS and this confirmed that the reaction mixture contained the desired product, bis-acid chloride' and 'bis-N-diallylamide'. Once the reaction was deemed complete, the solution was filtered, vacuumed to dryness, then dissolved in 500 ml of ethyl acetate this solution is then loaded onto silica and purified on a 750 g column using ethyl acetate (B) and petrol (A) (10%→100% B over ~10 column volumes). The pure fractions are collected and identified by TLC, the desired fractions are then vacuumed to dryness. The structure was confirmed by $^1$H NMR and purity by LCMS (656.82 (+ve))

b) Synthesis of acetic acid (3-allylcarbamoyl-5-chlorocarbonyl-2,4,6-triiodo-phenylcarbamoyl)-methyl ester (10)

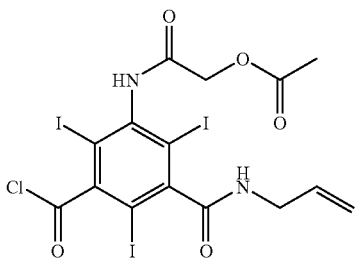

(10)

3-Allylcarbamoyl-5-amino-2,4,6-triiodo-benzoyl chloride (6) (5 g, 8.11 mmol) was dissolved in dry DMA (5 mL) and acetoxyacetylchloride (1.73 mL, 16.2 mmol) was added. The reaction was stirred overnight at room temperature with nitrogen bubbling through. The reaction mixture was diluted with ethyl acetate (100 mL) and washed with ice-water (5×20 mL). The organics were collected, dried over MgSO$_4$, filtered and evaporated to dryness under reduced pressure. The residue was washed with acetonitrile, filtered and dried under vacuum to give acetic acid (3-allylcarbamoyl-5-chlorocarbonyl-2,4,6-triiodo-phenylcarbamoyl)-methyl ester as a white solid. (4.47 g, 77%). The structure was confirmed by $^1$H and $^{13}$C NMR, and purity by LCMS.

c) Synthesis of acetic acid [3-(allyl-methyl-carbamoyl)-5-chlorocarbonyl-2,4,6-triiodo-phenylcarbamoyl]-methyl ester (11)

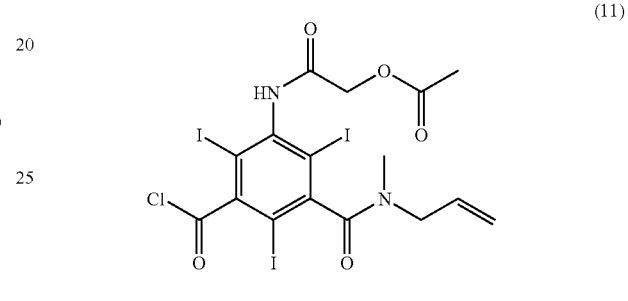

(11)

3-(Allyl-methyl-carbamoyl)-5-amino-2,4,6-triiodo-benzoyl chloride (8) (5 g, 7.93 mmol) was dissolved in dry DMA (20 mL) was acetoxyacetyl chloride (1.7 mL, 15.9 mmol) was added dropwise. The reaction mixture was stirred at overnight at RT, with nitrogen bubbling through the reaction mixture. The reaction was monitored by TLC on silica gel plates eluting with ethyl acetate: petrol (1:1). (6) had an Rf of 0.62 and 0.76 whilst there were two new spots at 0.32 and 0.22. The solution was diluted with ethyl acetate (~100 mL) and washed with ice water/brine (50:50, 20 ml×5). The organics were dried over MgSO4, filtered, concentrated and dried under high vacuum to give the desired compound (5.26 g, 91%). The structure was confirmed by $^1$H and $^{13}$C NMR, and purity by LCMS.

d) Synthesis of acetic acid (3-chlorocarbonyl-5-diallylcarbamoyl-2,4,6-triiodo-phenylcarbamoyl)-methyl ester (12)

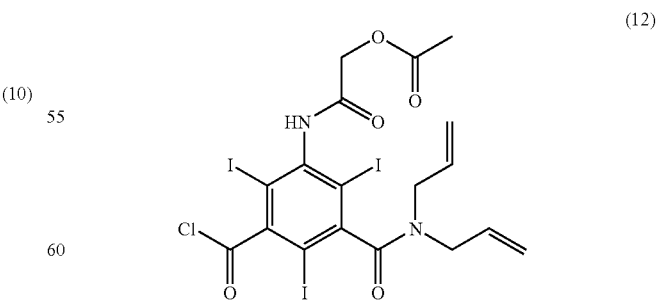

(12)

The mono-diallylamide (9) (6.56 g, 10 mmol) was dissolved in anhydrous DCM (10 ml), and stirred. The acetoxy acetyl chloride (2.1 ml, 20 mmol) was added to the solution, and heated to 40° C. for 3 days. The solvent was removed at reduced pressure and the reaction mixture was absorbed onto silica gel. The crude mixture was separated by silica gel chromatography 10% EtOAc/Petrol=>100% EtOAc over 11 CVs. The main peak was collected, concentrated at reduced pressure and analysed by both LCMS (m/z 756.83 (+ve) and NMR. This indicated the desired material had been made in good purity. The yield was 6.5 g (86%).

e) Synthesis of lithium 2,3-dihydroxypropanoate (13)

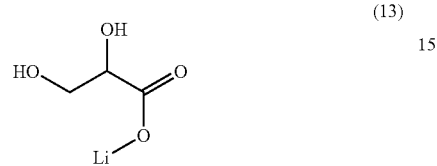

D,L-Serine (115.5 g, 1.10 mole) was added to a mixture of conc. sulfuric acid (75 g) in water (1.25 L) and the mixture was cooled to ca 5° C. Sodium nitrite (68.3 g, 0.99 mole) dissolved in water (500 ml) was added slowly during 3 h while temperature was kept at 5°-10° C. Then sulfuric acid (60 g) dissolved in water (200 ml) and cooled to ca 5° C. in a ice/water mixture, was added. A new portion of sodium nitrite (68.3 g, 0.99 mole) dissolved in water (500 ml) was added slowly during 2 h, while temperature was kept at 5°-10° C. The mixture was stirred at ambient temperature over night and then concentrated to a volume of ca 700 ml. Lithium hydroxide (22.7 g, 0.95 mole), dissolved in water (100 ml) was added. The mixture was now poured into a stirred mixture of methanol (1 L) and acetone (0.3 L). The precipitate formed was filtered off and washed with methanol/acetone (1/0.3 100 ml). The combined filtrates were now evaporated to a small volume (ca. 300 ml) and pH was adjusted to 7 by addition of a 5M solution of lithium hydroxide (ca. 200 ml). The mixture was evaporated to dryness and abs. ethanol (600 ml) was added, the product dissolved by heating and the mixture evaporated to dryness. The residue was then co evaporated twice with toluene (2×300 ml), and pumped in vacuo. There was of a gum like product 130 g. Identity was checked by $^1$H NMR in $D_2O$.

f) Synthesis of 2,3-diacetoxypropanoic acid (14)

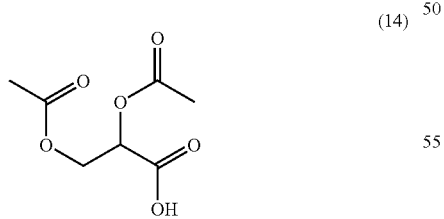

Acetyl chloride (500 ml) was added dropwise without stirring to the gummy like mass of lithium 2,3-dihydroxypropanoate (13) (171 g, 1.51 mole). The gummy like mass dissolved slowly and the mixture was left for 24 h at ambient temperature.

Then the mixture was stirred and heated to reflux for 6 h. After cooling the mixture was diluted with ethyl acetate (700 ml) and filtered through a tight glass filter (por. G4). The filtrate was evaporated to a oil, which was dissolved in ethyl acetate (750 ml) and washed with water (2×70 ml, pH=2). After drying over magnesium sulfate and treatment with activated charcoal (1.5 g) the mixture was filtered. The filtrate was evaporated to a light orange coloured oil. Yield (crude) 218 g (75%).

Purity checked by $^1$HNMR in $CDCl_3$.

g) Synthesis of 2,3-diacetoxypropanoyl chloride (15)

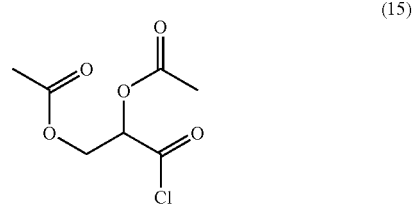

Thionyl chloride (62 ml, 0.86 mole) was added dropwise to 2,3-diacetoxypropanoic acid (14) in a flask to which a drop of N,N-dimethylformamide had been added. The mixture was then stirred at ambient temperature over night and then evaporated to a syrup at a temperature $\leq 40°$ C. The syrup was taken up in diethyl ether (60 ml) and activated charcoal (0.3 g) added. The mixture was then filtered through a tight glass filter and evaporated in vacuo (10 torr). The oily residue was distilled in a Kugelrohr apparatus to give 24.6 g (68%). Identity and purity checked by $^1$HNMR in $CDCl_3$.

h) Synthesis of acetic acid 2-acetoxy-2-(3-allylcarbamoyl-5-chlorocarbonyl-2,4,6-triiodo-phenylcarbamoyl)-ethyl ester (16)

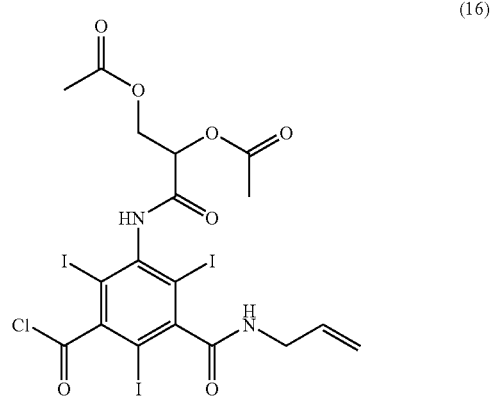

In dry three necked round bottom flask fitted with an additional funnel was poured 5 amino 2, 4, 6 triiodo isophthalic 3 ally amide (7) (10 g, 0.016 mol) and 10 ml of DMAC. To the stirred and cooled solution 1, 3 acetate 4 carbonyl chloride 2, 2 dimethyl (15) (6.8 g, 0.032 mol) in 10 ml of DMAc was added dropwise over 15-20 minutes. The reaction was allowed to react 20 hours with a gentle flow of nitrogen bubbling through the reaction. The solvent was concentrated under vacuo and the resulting dark brown crude mixture was purified via normal phase column chromatography eluting with ethyl acetate and petroleum ether. After purification 11 g of an off-white solid was obtained (90% yield and 98% HPLC purity)

Mass found: (ES+) 789, 811 (Na+) and 1576.64, (ES−) 787, 1574 i) Synthesis of acetic acid 2-acetoxy-2-[3-(allyl-methyl-carbamoyl)-5-chlorocarbonyl-2,4,6-triiodo-phenylcarbamoyl]-ethyl ester (17)

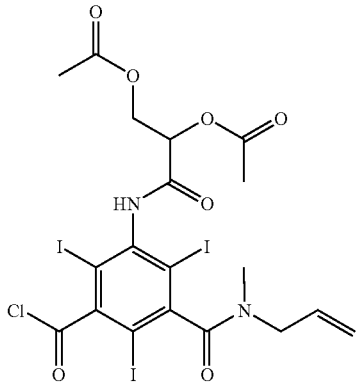

(17)

3-(Allyl-methyl-carbamoyl)-5-amino-2,4,6-triiodo-benzoyl chloride (8) (0.19 mol, 120 g) was dissolved in dry N,N-dimethyl acetamide (DMA) (480 ml) and the acid chloride (10) (0.38 ml, 79 g) was added dropwise. The clear yellow red reaction mixture was stirred at overnight at ambient temperature, with nitrogen bubbling through the reaction mixture. The reaction was monitored by TLC on silica gel plates eluting with ethyl acetate: petrol (1:1). After 19 hours the reaction was stopped and the brown solution was diluted with ethyl acetate (~2.4 L) and washed with ice water/brine (50:50, 480 ml×5). The filtrate was washed again with ethyl acetate. 500 ml of filtrate washed twice with 250 ml of ethyl acetate. The brown solution was poured into a 6 L separating funnel and treated with 200 ml of cold water/brine (1:1) solution. The organics were dried over MgSO$_4$, filtered and concentrated. The brown oil obtained was dried under high vacuum over night and analysed via LCMS. One major peak was observed with a mass of 803 (M+H+) and a purity of 86%. $^1$H NMR was carried out (CDCl$_3$). The NMR spectrum showed residual ethyl acetate. The brown oil was left under high vacuum at 40° C. for 1 hour and then left over night under high vacuum at ambient temperature. The mixture was dissolved in ethyl acetate and supported onto silica gel and purified by silica gel chromatography eluting with ethyl acetate/petrol. The off white solid was dried over night under high vacuum at room temperature and this gave a yield of 56%. LCMS was carried out Luna C18 250×4.6 10 u. Purity 95%, $^1$H NMR (CDCl$_3$) confirmed structure of the desired compound.

j) Synthesis of acetic acid 2,3-diacetoxy-3-chlorocarbonyl-propyl ester (18)

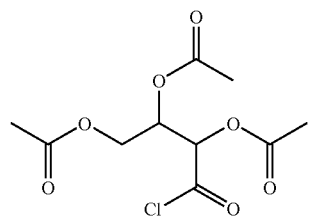

(18)

The 2,3,4-triacetoxy-butyric acid (25 g, 0.095 mol) was stirred in thionyl chloride (15.3 mL) at room temperature with a condenser fitted. The reaction was stirred for 48 hours and then the thionyl chloride was removed under reduced pressure to give an oil which was the desire material (26.1 g, 98%).

k) Synthesis of acetic acid 2,3-diacetoxy-1-(3-allyl-carbamoyl-5-chlorocarbonyl-2,4,6-triiodo-phenylcarbamoyl)-propyl ester (19)

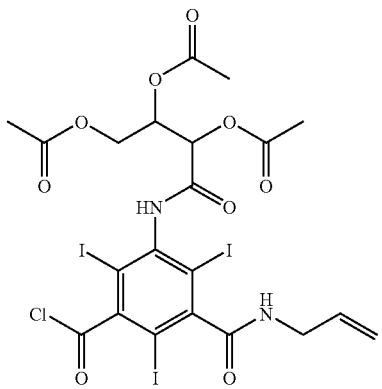

(19)

3-Allylcarbamoyl-5-amino-2,4,6-triiodo-benzoyl chloride (7) (20 g, 32.4 mmol) was dissolved in dry DMA (50 mL) and threonic acid chloride triacetate (18) (18.22 g, 64.8 mmol) was added. The reaction was stirred for 3 days at room temperature with nitrogen bubbling through. The reaction mixture was diluted with ethyl acetate (100 mL) and washed with ice-water (5×20 mL). The organics were collected, dried over MgSO$_4$, filtered and evaporated to dryness under reduced pressure. The solid was adsorbed onto silica gel and purified by column chromatography eluting with DCM: ethyl acetate (0-100%, SiO$_2$, 750 g, 10 CV) to give acetic acid 2,3-diacetoxy-1-(3-allylcarbamoyl-5-chlorocarbonyl-2,4,6-triiodo-phenylcarbamoyl)-propyl ester as a yellow solid (15.1 g, 54%).

l) Synthesis of acetic acid 2,3-diacetoxy-1-[3-(allyl-methyl-carbamoyl)-5-chlorocarbonyl-2,4,6-triiodo-phenylcarbamoyl]-propyl ester (20)

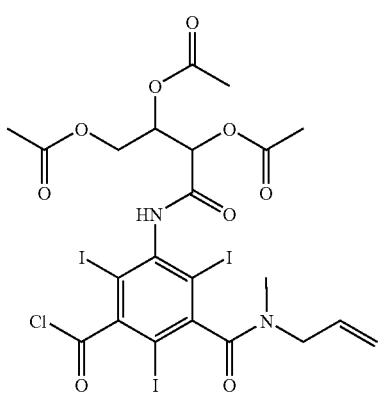

(20)

5-amino-2,4,6-triiodoisophathalic mono-N-methyl allylamide (8) (13.5 g, 0.0214 mol) and threonic acid chloride triacetate (18) (11.1 g, 0.0395 mol) were dissolved in dry dimethylacetamide (60 mL) and stirred for 48 hours at room temperature. The reaction mixture was diluted with ethyl acetate (250 mL) and washed with ice-water/brine (50:50, 5×25 mL). The organics were collected and dried over $MgSO_4$, filtered and evaporated to dryness to give a brown oil. It was purified by column chromatography, eluting with petrol: ethyl acetate (10-100%, 12 column volumes, $SiO_2$, 330 g) to give the desired product as an off white solid (10.1 g, 54%).

The product was confirmed by $^1H$ NMR ($CDCl_3$).

n) N N',N"-Tris[(3-N-Methyl-allylcarbamoyl-2,4,6-triiodo-1-acetoxyacetamide) phenyl]carbamoyl methyl ethane

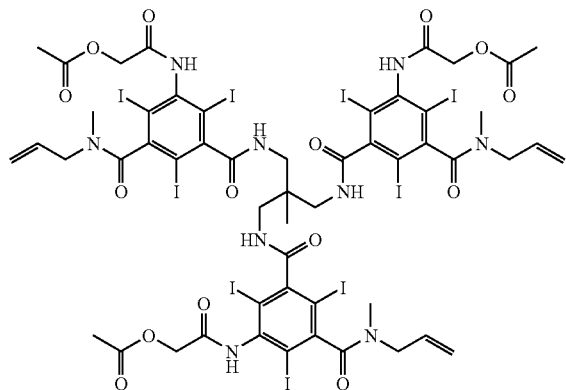

To a solution of 2-Aminomethyl-2-methyl-propane-1,3-diamine (195 mg, 1.63 mmol) cooled to a 0° C. in dimethyl amino acetamide (0.5 ml) were added Acetic acid [3-(allyl-methyl-carbamoyl)-5-chlorocarbonyl-2,4,6-triiodo-phenyl-carbamoyl]-methyl ester (3.65 g, 4.9 mmol) and triethylamine (0.505 g, 5 mmol)). The reaction mixture was allowed to react under nitrogen for 18 hrs. Triethylamine was removed under high vacuum below 40° C., 100 ml of water was added and the resulting precipitate was isolated via filtration. The crude mixture was purified via silica gel chromatography eluting with methanol:ethyl acetate (1:9 to 3:7). This yielded a white solid (47%) which was the titled compound.

MS (ES+) m/2=1100.17 $[M+H]^+$ $^1H$ NMR ($DMSOd_6$): 10.2 (t, 3H), 8.73-8.30 (3H, vBr); 5.89 (3, m); 5.43 (3, dd); 5.28 (3, dd); 4.68 (6, m); 4.08 (3H), 3.75-3.15 (12H, vBr); 2.92 (3H), 2.72 (3H), 2.14, (9, s); 1.20 (3, s).

Further compounds were prepared in an analogous manner: N,N',N"-Tris[(3-N-Methyl-allylcarbamoyl-2,4,6-triiodo-(2,3-dihydroxy-propionylamino) phenyl) carbamoyl methyl ethane using acetic acid 2-acetoxy-2-(3-allylcarbamoyl-5-chlorocarbonyl-2,4,6-triiodo-phenylcarbamoyl)-ethyl ester and N,N',N"-Tris[(3-N-Methyl-allylcarbamoyl-2,4,6-triiodo-(2,3,4-trihydroxy-butyrylamino) phenyl) carbamoyl methyl ethane using acetic acid 2,3-diacetoxy-1-[3-(allyl-methyl-carbamoyl)-5-chlorocarbonyl-2,4,6-triiodo-phenyl-carbamoyl]-propyl ester o) N,N',N"-Tris[(3(N-methyl-2,3,dihydroxypropyl-carbamoyl)-2,4,6-triiodo-1-acetoxy acetamide) phenyl]carbamoyl methyl ethane

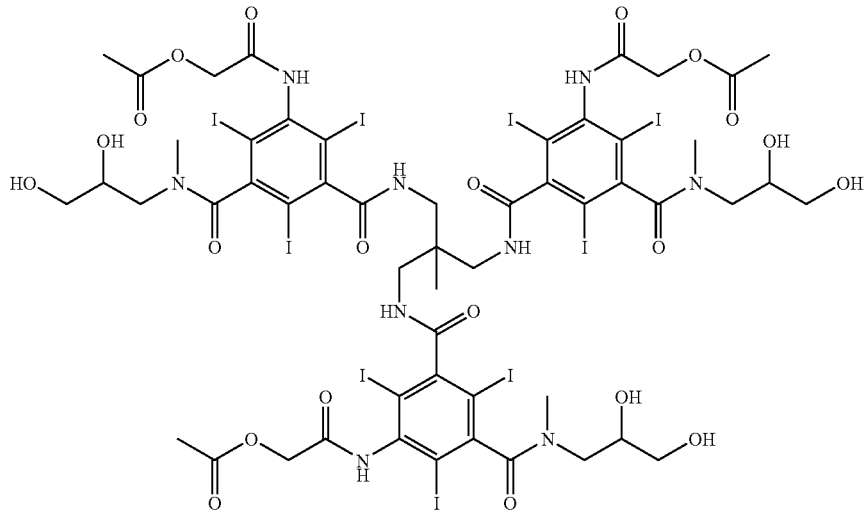

N,N',N''-Tris[(3-allylcarbamoyl-2,4,6-triiodo-1-acetoxy-acetamide)phenyl] carbamoyl methyl ethane (2.70 g, 1.2 mmol) was dissolved in a mixture of acetone/water (9/1) (20 mL). A solution of osmium catalyst (2 mL) (1 g OsO4, 100 ml t-BuOH 100 ml and 10 drops of t-BuOOH) was added followed by addition of N-methylmorpholine oxide (850 mg). The mixture was stirred over night at ambient temperature. After quenching the reaction with a 10 ml solution of sodium hydrogen sulphite (15%) the mixture was evaporated to dryness. The crude was used without further purification.

MS (ES+) m/2=1151.41 [M+H]$^+$ p) N,N',N''-Tris[(3(N-methyl-2,3,dihydroxypropyl-carbamoyl)-2,4,6-triiodo-(2,3-dihydroxy-propionylamino)phenyl) carbamoyl methyl ethane and N,N',N''-Tris[(3(N-methyl-2,3,dihydroxypropylcarbamoyl)-2,4,6-triiodo-(2,3,4-trihydroxy-butyrylamino) phenyl) carbamoyl methyl ethane N,N',N''-Tris-[(3(N-methyl-2,3-dihydroxypropylcarbamoyl)-2,4,6-triiodo-1-hydroxyl acetamide) phenyl] carbamoyl methyl ethane

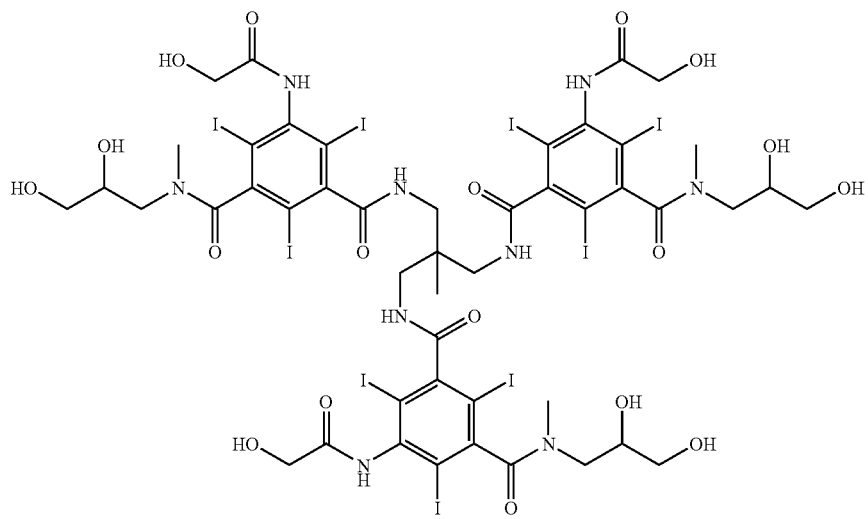

N,N',N''-Tris[(3(N-methyl-2,3,dihydroxypropylcarbamoyl)-2,4,6-triiodo-1-acetoxy acetamide) phenyl] carbamoyl methyl ethane (1.50 g, 6.5 mmol) was dissolved in methanol (5 mL). Sodium methoxide (30 mg) was added to the solution and was stirred overnight. A white precipitate was formed which was collected by filtration. The crude material was purified using preparative HPLC. The required fractions were concentrated and freeze dried. This yielded a white solid (700 mg) which was found to be the desired compound.

MS (ES+) m/2=1088.36 [M+H]$^+$

EXAMPLE 6

N,N',N''-Tris-[(3(N-methyl-2,3-dihydroxypropylcarbamoyl)-2,4,6-triiodo-(2,3-dihydroxy-propionylamino) phenyl) carbamoyl methyl ethane This compound was prepared in a similar manner as in Example 5 above.

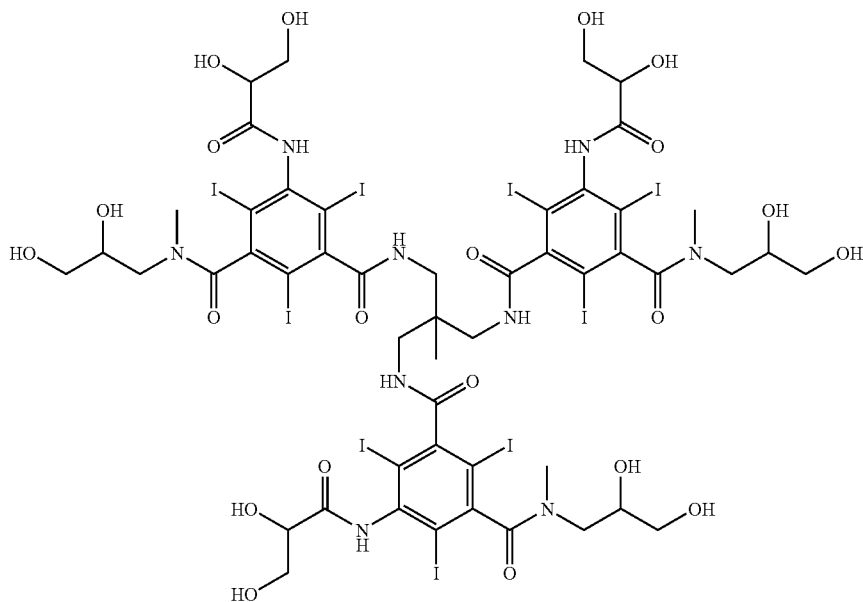

MS (ES+) m/2=1133.6 [M+H]$^+$

EXAMPLE 7

N,N',N''-Tris-[(3(N-2,3-dihydroxypropylcarbamoyl)-2,4,6-triiodo-(2,3,4-trihydroxy-butyrylamino) phenyl) carbamoyl methyl ethane This compound was prepared in similar manner as Example 5 above.

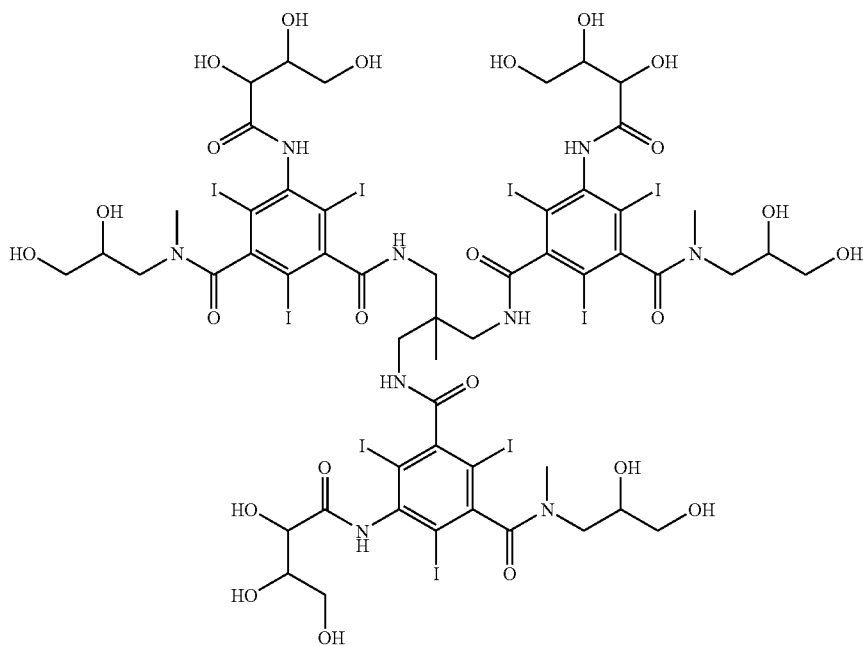

MS (ES+) m/2=1178.47 [M+H]$^+$

EXAMPLE 8

N,N',N"-Tris-[(3(N-2,3-dihydroxypropylcarbamoyl)-2,4,6-triiodo-1-hydroxyl acetamide) phenyl] carbamoyl methyl ethane

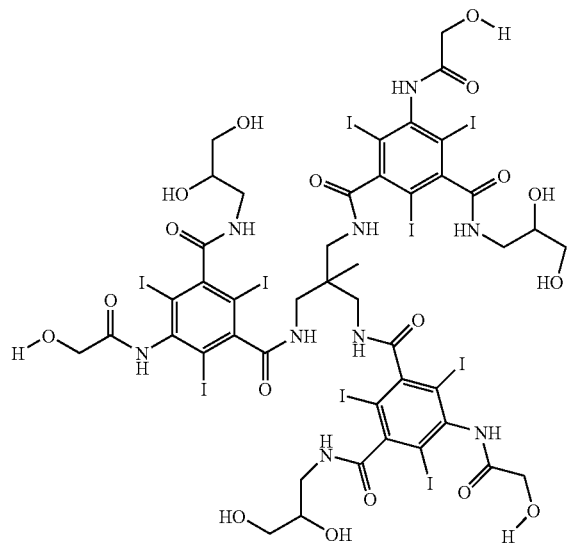

Starting material and all other materials were commercially available from Aldrich.

a) 5-amino-2,4,6-triiodo-isophthaloyl chloride

5-Amino-2,4,6-triiodo-isophtalic acid (30 g, 0.054 mol), thionyl chloride (8.2 ml, 0.113 mol) and pyridine (0.2 ml) in 1,2 dichloroethane (20 ml) were heated to 70° C. A portion of thionyl chloride (15.2 ml, 0.21 mol) was added dropwise during 1½ to 2 hrs, and the mixture was heated to 85° C. for 6 hrs. After cooling the reaction mixture to room temperature, it was poured into 300 g of ice-water. The yellow precipitate that formed was filtered off, sucked dry and then washed with water until washings showed a pH of ca 5. The filter cake was then dried in a vacuum oven at 50° C. for 3 hrs. A light yellow powder was obtained 31 g (~quant.) as the desired product.

$^{13}$C NMR (DMSOd$_6$) 66, 78.4, 148.9, 149.2, 169
MS (ES−) found 593.5 [M-H+], expected 593.7
FT-IR (cm$^{-1}$) 3471, 3372 (NH), 1777 (C=O).
Literature: Bioorganic Medicinal Chemistry, Vol. 10, (2002), 3545-3554 b) 5-acetoxy acetamide 2,4,6,triiodo-isophthaloyl chloride

To a brown suspension of 5-amino-2,4,6-triiodo-isophthaloyl chloride (35 g, 0.06 mol) in THF (42 ml) was added acetoxy acetyl chloride (12.7 ml, 0.118 mol) at room temperature and under a flow of nitrogen. The solution was heated over night under reflux. Heptane (84 ml) was poured into the solution and the mixture was heated again under reflux for 30 minutes. The reaction mixture was cooled down to room temperature. Isolation of a light brown solid was carried out via filtration which was recrystallised using THF/Heptane. The off white powder was dried under high vacuum over night to give 12 g. (35%) of the title compound $^1$H NMR (DMSOd$_6$): 2.1 (s, 3H); 4.6 (s, 2H)
TLC: 0.43 (EtOAc-Pet Ether (60:40))
MS (ES−) Found 694.08 (M-H+) 93% purity by HPLC c) N(3-allylcarbamoyl-5-chlorocarbonyl-2,4,6-triiodo-phenyl)-1-acetoxy acetamide In a dried three necked round bottom flask, a solution of 5-acetoxy acetamide 2, 4,6,triiodo-isophthaloyl chloride (8.5 g, 12.2 mmol) in dry N,N dimethyl acetamide (100 ml) and triethylamine (2 ml, 12.2 mmol) was treated with allyl amine (1 ml, 13.6 mmol) at ambient temperature for 16 hours under a gentle flow of nitrogen.

Triethylamine was removed under high vacuum, water was added to precipitate a solid, which was collected by filtration. The solid was purified by column chromatography in a gradient 5-60% ethyl acetate/hexane on silica. The fractions eluting in 50% ethyl acetate were collected, concentrated to give a white powder. 5.6 g was obtained (64%) of the title compound.

$^1$H NMR (DMSOd$_6$): 2.15 (s, 3H); 3.89 (br s, 1H); 4.70 (s, 2H); 5.15-5.4 (2H dd); 5.89 (m, 1H); 8.79-9.03 (1H, dd); 10.3 (s, 1H)
MS (ES−) Found 715 (M-H+)
96.5% purity by HPLC d) N,N',N"-Tris[(3-allylcarbamoyl-2,4,6-triiodo-1-acetoxyacetamide) phenyl]carbamoyl methyl ethane To a solution of 2-Aminomethyl-2-methyl-propane-1,3-diamine (45.2 mg, 0.4 mmol) cooled to a 0° C. in dimethyl amino acetamide (0.5 ml) were added N(3-allylcarbamoyl-5-chlorocarbonyl-2,4,6-triiodo-phenyl-1-acetoxy acetamide) (884 mg, 1.23 mmol) and triethylamine (0.18 ml, 1.3 mmol)). The reaction mixture was allowed to react under nitrogen for 48 hrs. Triethylamine was removed under high vacuum below 40° C., 100 ml of water was added and the resulting precipitate was isolated via filtration. The crude mixture was purified via preparative HPLC: Column Gemini C$_{18}$, 1 50×21.2, Flow 21 ml/min, Solvents: A Water/0.1% formic acid, B: acetonitrile, Detection 254 nm, Gradient 5-95% in 12 minutes solvent B, The desired fractions tr=7.4 minutes were collected and freeze dried over night to give 267 mg as white solid (32%) of the title compound.

MS (ES+) m/z=2179 [M+23]+; 2157 [M+H+],
$^1$H NMR (DMSOd$_6$): 10.2 (d, 3H, 8.7-8.8 (3H, d); 5.9 (3, m); 5.4 (3, dd); 5.1 (3, dd); 4.6 (6, m); 3.8 (6, s); 2.1, (9, s); 1.2 (3, s).

e) N,N',N"-Tris[(3(N-2, 3, dihydroxypropylcarbamoyl)-2,4,6-triiodo-1-acetoxy acetamide) phenyl] carbamoyl methyl ethane N,N',N"-Tris[(3-allylcarbamoyl-2,4,6-triiodo-1-acetoxyacetamide)phenyl] carbamoyl methyl ethane (250 ml, 0.116 mmol) was dissolved in a mixture of acetone/water (9/1). 0.23 ml of a solution of osmium catalyst (1 g OsO4, 100 ml t-BuOH 100 ml and 10 drops of t-BuOOH) was added followed by addition of N-methylmorpholine oxide (54 mg). The mixture was stirred over night at ambient temperature. After quenching the reaction with a 10 ml solution of sodium hydrogen sulphite (15%) the mixture was evaporated to dryness. The crude was purified via HPLC semi preparative Gemini 21.2×150 mm C$_{18}$ column, Detection 254 nm, Flow 21 ml/min, Solvent A: 01% formic acid/Water, Solvent B: Acetonitrile, Gradient 0-95% over 12 minutes solvent B, Fractions at tr=5.5 minutes were isolated as the desired product.

75 mg as white powder was obtained (28.6%) of the title compound.

MS (ES+) m/z=2259 [M+H]+, 2241 [M-18]+ and 2281 [M+Na+]+

$^1$H NMR (D$_2$O): 1.27 (s, 3H); 2.2 (s, 9H); 3.3-0.7 (m, 22); 4 (m, 3); 4.7 (s, 2H)

98% purity by HPLC f) N,N',N''-Tris-[(3(N-2,3-dihydroxypropylcarbamoyl)-2,4,6-triiodo-1 hydroxy acetamide) phenyl]carbamoyl methyl ethane N,N',N''-Tris[(3(N-2,3,dihydroxypropylcarbamoyl)-2,4,6-triiodo-1-acetoxy acetamide) phenyl] carbamoyl methyl ethane (10 mg, 0.004 mmol) was dissolved in methanol (1.7 ml). Triethylamine (0.05 ml) was added dropwise to the clear solution and the mixture was allowed to react over night (18 hrs). A small aliquot was taken out of the reaction, concentrated via speed vac and analysed via HPLC. The reaction was not complete. The mixture was heated up to 40° C. for two hours until HPLC analysis confirmed the completion of the reaction. The mixture was concentrated under speed vacuum to give 90 mg of the title compound.

$^1$H NMR (D$_2$O): 1.27 (s, 3H); 3.3-0.7 (m, 22); 4 (m, 3); 4.7 (s, 2H)

MS (ES+) m/z=2133.6 [M+H+]; 2115.6 [M-18]+; 2155.7 [M+Na]+

97% purity by HPLC

Following the procedures above, the compounds of Examples 9 to 21 were prepared:

EXAMPLE 9

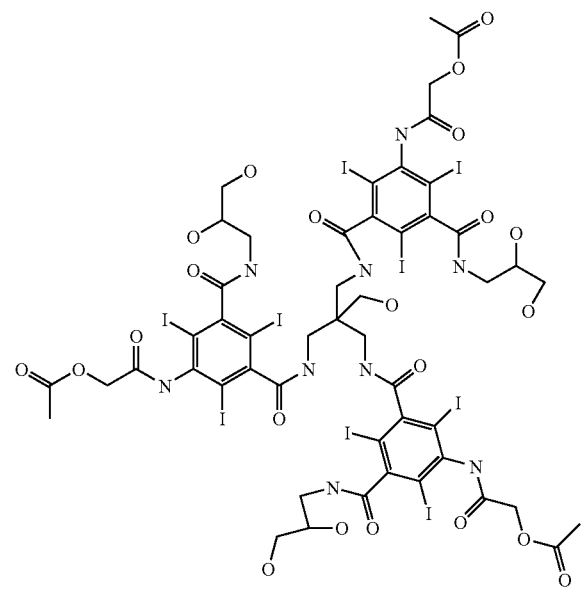

MS (ES+) found 1136.88 [M/2+H+]

EXAMPLE 10

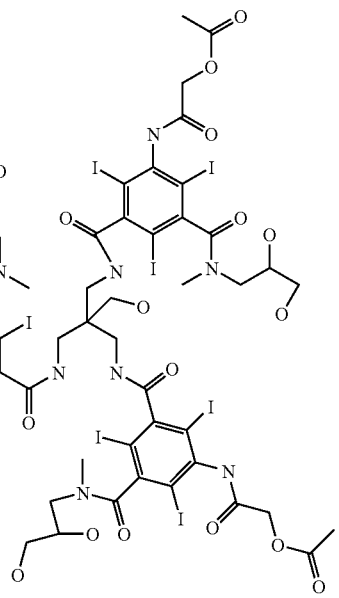

EXAMPLE 11

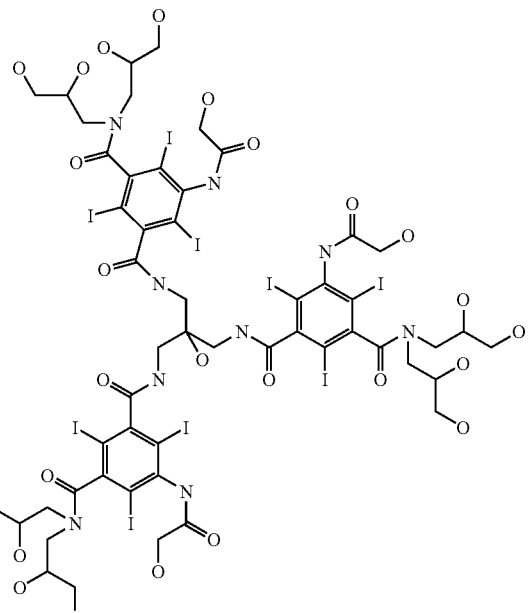

MS (ES+) found 1179.36 [M/2+H+]

61
EXAMPLE 12
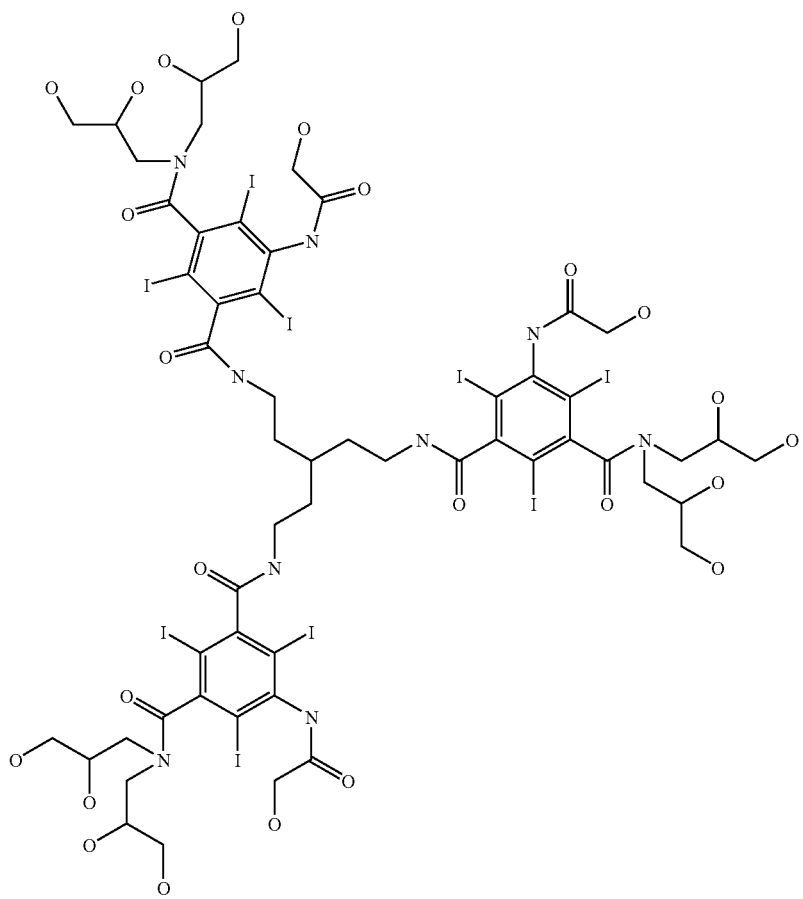
MS (ES+) found 1192.38 [M/2+H+]
EXAMPLE 13
EXAMPLE 14
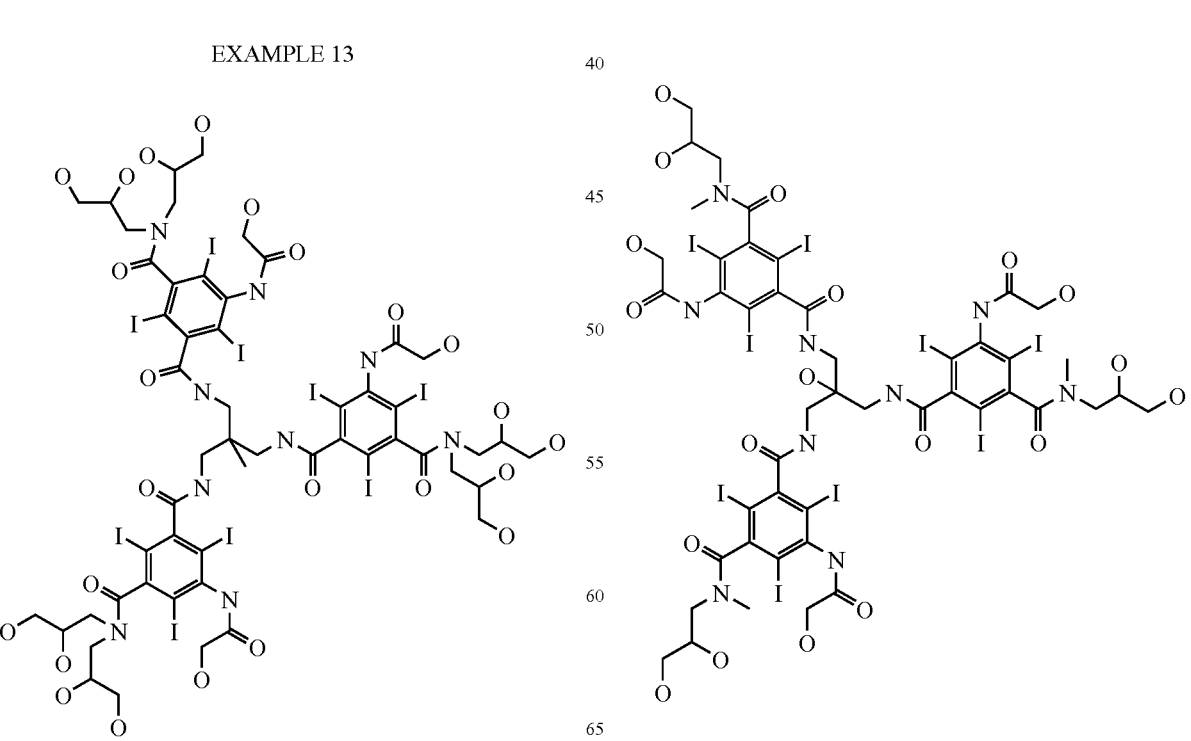
MS (ES+) found 1178.57 [M/2+H+]
MS (ES+) found 1089.44 [M/2+H+]

EXAMPLE 15
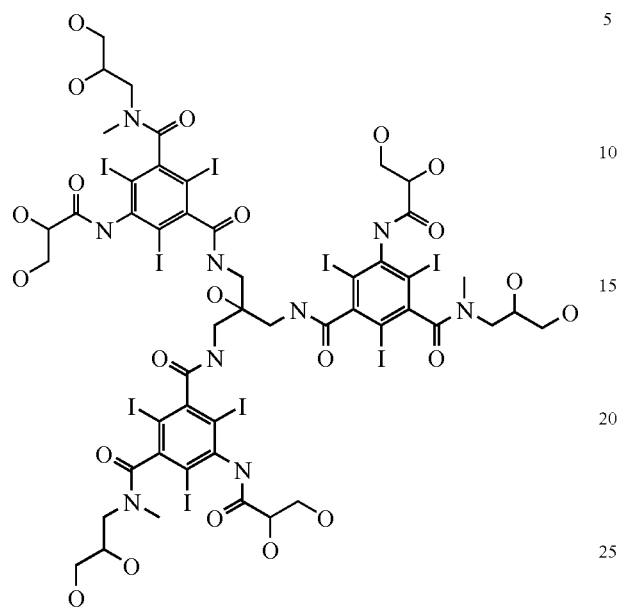
MS (ES+) found 1134.36 [M/2+H+]
EXAMPLE 16
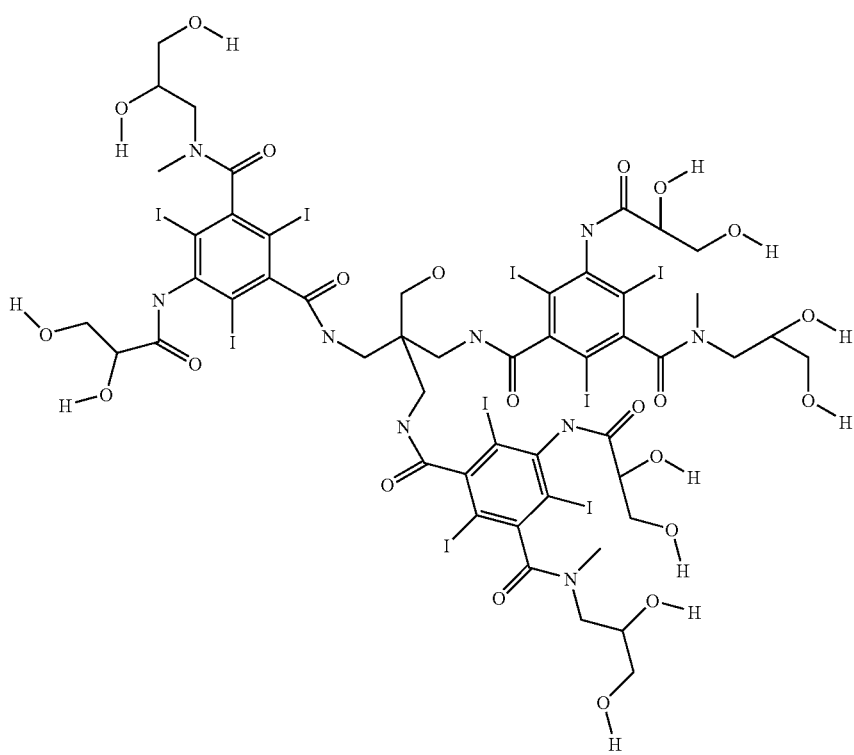
MS (ES+) found 1102.42 [M/2+H+]

EXAMPLE 17
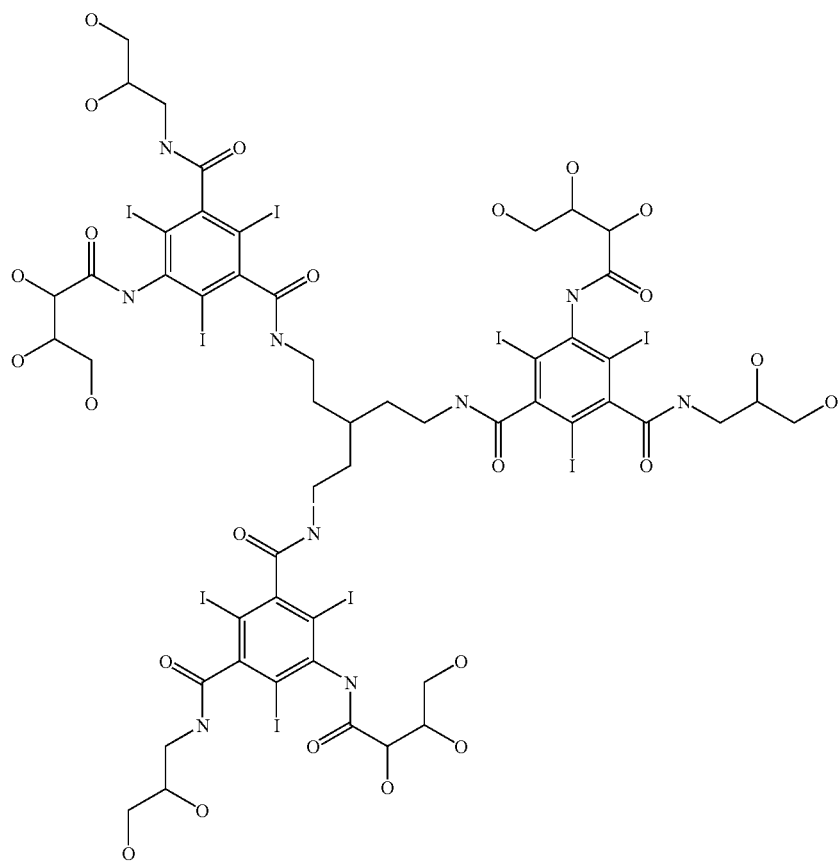
MS (ES+) found 1171.33 [M/2+H+]
EXAMPLE 18
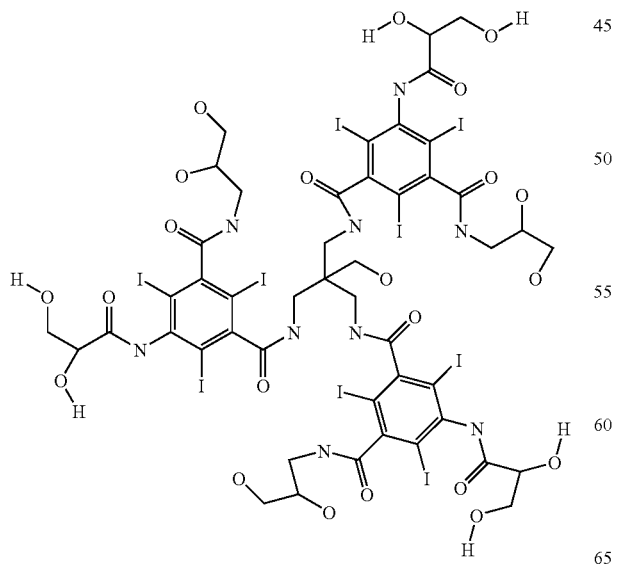
MS (ES+) found 1120.25 [M/2+H+]

EXAMPLE 19
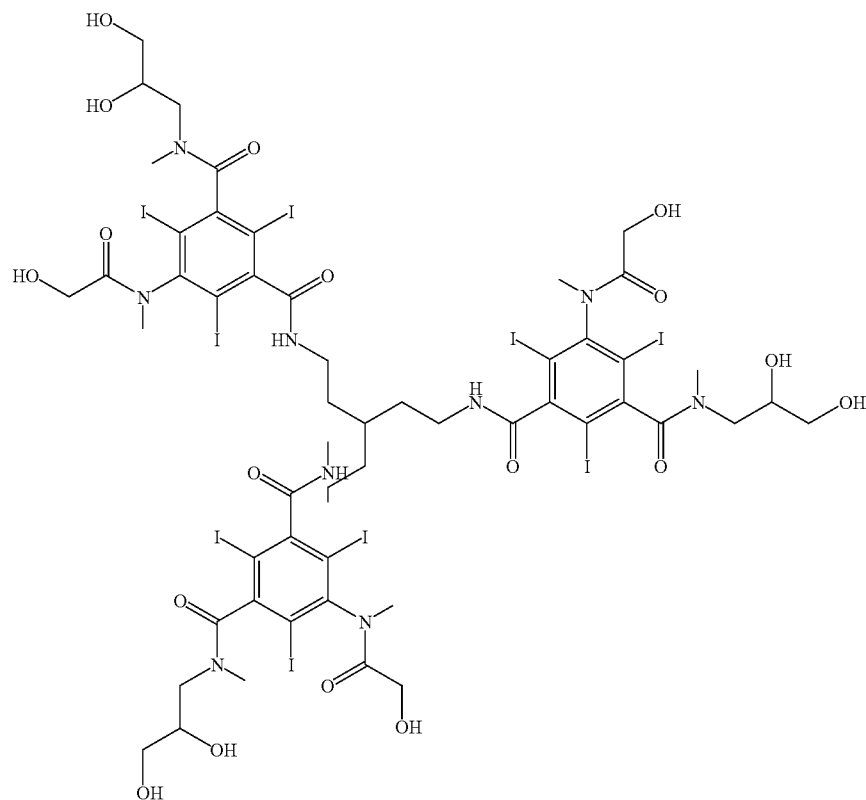
MS (ES+) found 1123.18 [M/2+H+]
EXAMPLE 20
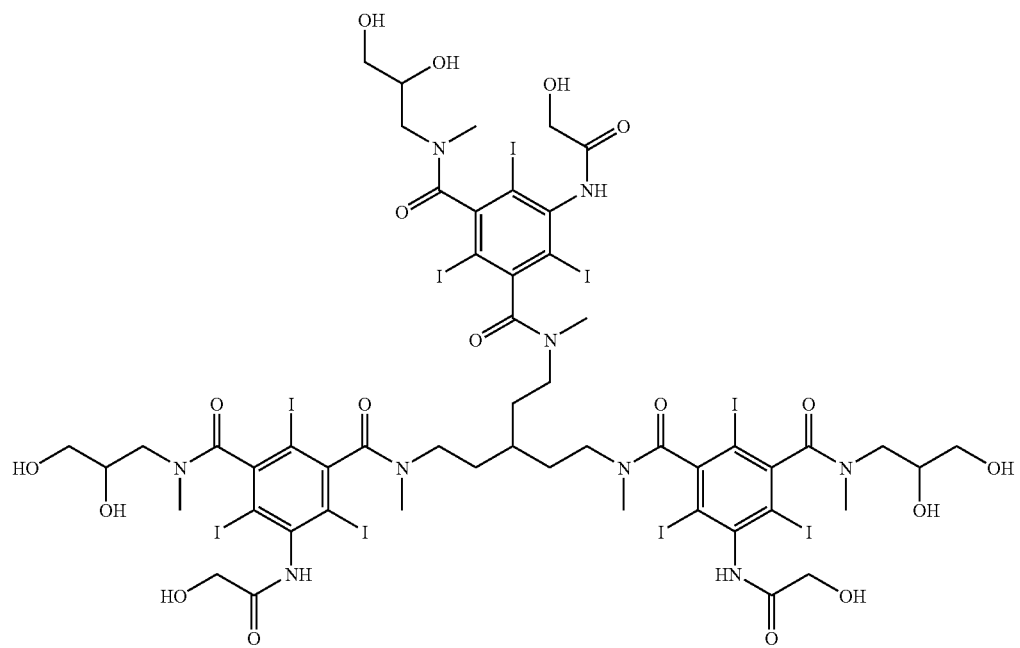
MS (ES+) found 1123.33 [M/2+H+]

EXAMPLE 21

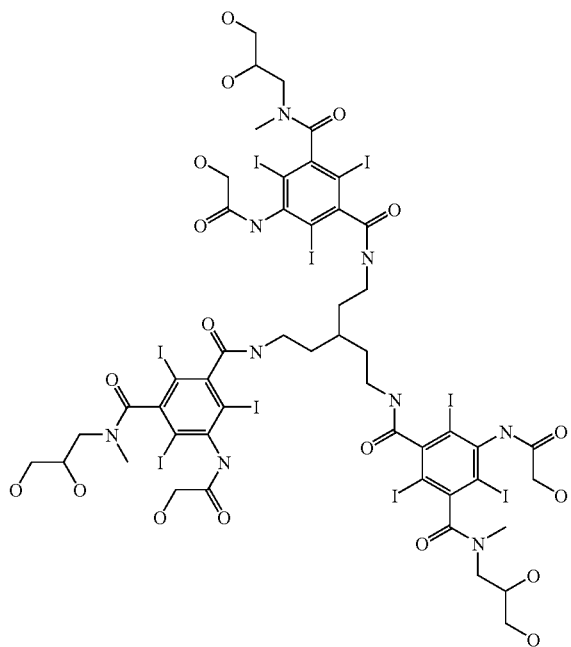

MS (ES+) found 1102.5 [M/2+H+]

EXAMPLE 22

N1,N6-Bis-[2-(N-(2,3-dihydroxy-propyl)-5-(2-hydroxy-acetylamino)-2,4,6-triiodo-isophthalylamino)-hexyl]-N4'-(2,3-dihydroxy-propyl)-5-(2-hydroxy-acetylamino)-2,4,6-triiodo-isophthalamide a) 3-ethoxycarbonylhexanedioic acid diethyl ester

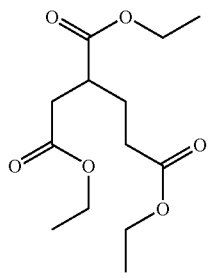

To an ethanolic solution of 3-carboxyhexanedioic acid (10 g) was added a few drops of conc. sulphuric acid. The mixture was heated at reflux for 24 hours. After Aqueous work up and extraction in to DCM concentration of the dried organic layer yielded a clear oil. This was found to be 3-ethoxycarbonyl-hexanedioic acid diethyl ester by NMR in quantitative yield.

b) 3-Hydroxymethyl-hexane-1,6-diol

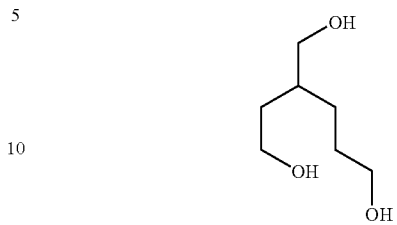

To a solution of 3-ethoxycarbonylhexanedioic acid diethyl ester (10 g, 0.036 mol) in tert-butanol (100 mL) was added sodiumborohydride (6 g). The mixture was heated to reflux. Methanol (10 mL) was added in 3 aliquots over 30 minutes. The solution was heated at reflux for a further 30 minutes and allowed to cool. The solution was neutralised with 5 M hydrochloric acid with care. The solution was filtered and extracted with ethanol (2×50 mL). The solutions were combined and the solvent was removed at reduced pressure. The residue was extracted with ethanol (60 mL), filtered and concentrated at reduced pressure to yield the desired product as a clear, colourless liquid. This was analysed by NMR in $D_2O$ and found to be 3-hydroxymethylhexane-1,6-diol in a yield of 4.5 g (85%).

c) Toluene-4-sulfonic acid 6-tosyloxy-4-tosyloxymethyl-hexyl ester

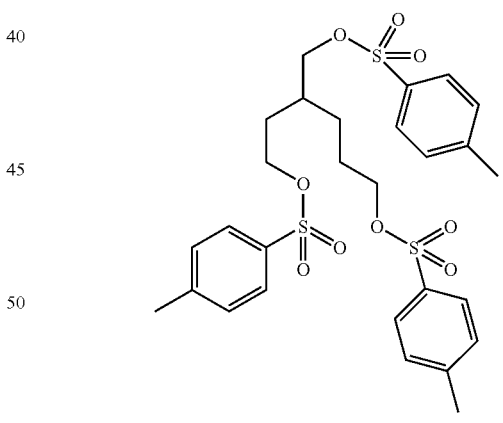

To a solution of 3-hydroxymethylhexane-1,6-diol (4 g, 0.027 mol) in pyridine (80 mL) stirred in an ice bath was added para-toluenesulphonyl chloride (16.9 g, 0.09 mol) in one portion. The mixture was allowed to warm to ambient temperature. After 48 hours the reaction was worked up using DCM (100 mL) which was washed with 1N HCl (2×100 mL). The organic layer was dried and concentrated to yield a very viscous, sticky oil which was analysed by NMR. This confirmed the desired material had been formed in a yield of 60% (9.9 g). The material was used without further purification.

d) N1,N6-Dibenzyl-3-[(benzyl-methyl-amino)-methyl]-N1,N6-dimethylhexane-1,6-diamine

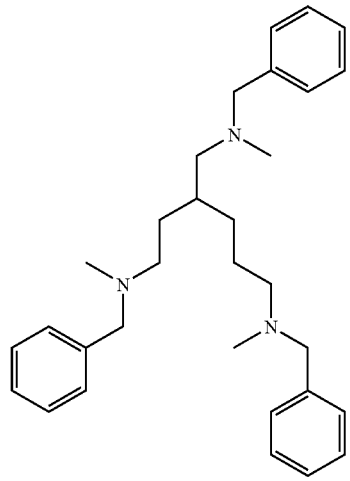

To a solution of toluene-4-sulfonic acid 6-tosyloxy-4-tosyloxymethyl-hexyl ester (4.5 g, 0.0073 mol) in THF (20 mL) was added N-benzylmethylamine (8.8 g, 0.073 mol) in one portion. The mixture was heated at reflux. After 48 hours the reaction was cooled and filtered leaving a yellow filtrate. The filtrate was concentrated and adsorbed onto silica gel. The mixture was separated on a 120 g silica gel column eluting with methanol/DCM (2:98=>10:90). This yielded N1,N6-Dibenzyl-3-[(benzyl-methyl-amino)-methyl]-N1,N6-dimethylhexane-1,6-diamine in a yield of 53% (1.77 g). The structure was confirmed by NMR.

e) N1,N6-Dimethyl-3-methylaminomethylhexane-1,6-diamine

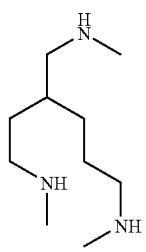

To a methanolic solution of N1,N6-Dibenzyl-3-[(benzyl-methyl-amino)-methyl]-N1,N6-dimethylhexane-1,6-diamine (1 g, 0.002 mol) was added 1 g of Pd/C. The solution was exposed to 2 bar of hydrogen and left to shake for 48 hours at ambient temperature. The reaction mixture was filtered through celite and concentrated at reduced pressure to yield a viscous oil. The structure was confirmed by NMR, yield ~90%.

f) Acetic acid (3,5-bis-chlorocarbonyl-2,4,6-triiodo-phenylcarbamoyl)-methyl ester

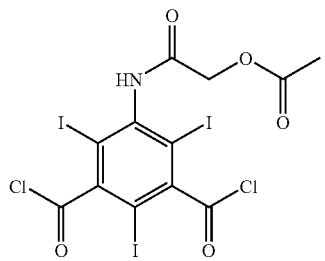

5-Amino-2,4,6-triiodo-isophthaloyl dichloride was dissolved in dimethyl acetamide (DAMC) and a solution of acetoxyacetylchloride (2 eq) in DMAc was slowly added with efficient stirring. The reaction mixture was stirred overnight and the following day, the mixture was slowly poured into stirred ice water. The precipitate was filtered off and dried to give the desired material. The structure was confirmed by $^1$H NMR (CDCl$_3$, 300 MHz): 10.43 (brs, 1H); 4.71 (s, 2H); 2.11 (s, 3H)

g) Acetic acid {3-chlorocarbonyl-5-[(2,3-dihydroxy-propyl)-methyl-carbamoyl]-2,4,6-triiodo-phenylcarbamoyl}-methyl ester

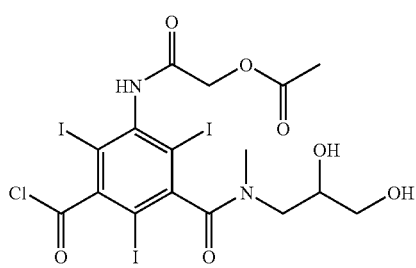

The bis-acid chloride from the previous step was dissolved in DMAC in a dry flask under a nitrogen atmosphere. Triethylamine (2 eq) was added to the solution immediately followed by the addition of 3-Methylamino-propane-1,2-diol (2 eq). After stirring overnight, the reaction mixture was concentrated to dryness, and the residue purified by chromatography using silica gel to give the desired product. The structure was confirmed by $^1$H NMR (DMSO-D6, 300 MHz): 10.4 (br s, 1H); 4.70 (s, 2H); 3.89-3.83 (m, 1H); 3.75-3.67 (m, 1H); 3.51-3.42 (m, 2H); 3.25-3.15 (m, 1H); 2.85 (s, 3H); 2.15 (s, 3H)

h) N1,N6-Bis-[2-(N-(2,3-dihydroxy-propyl)-5-(2-hydroxy-acetylamino)-2,4,6-triiodo-isophthalylamino)-hexyl]]-N4'-(2,3-dihydroxy-propyl)-5-(2-hydroxy-acetylamino)-2,4,6-triiodo-isophthalamide

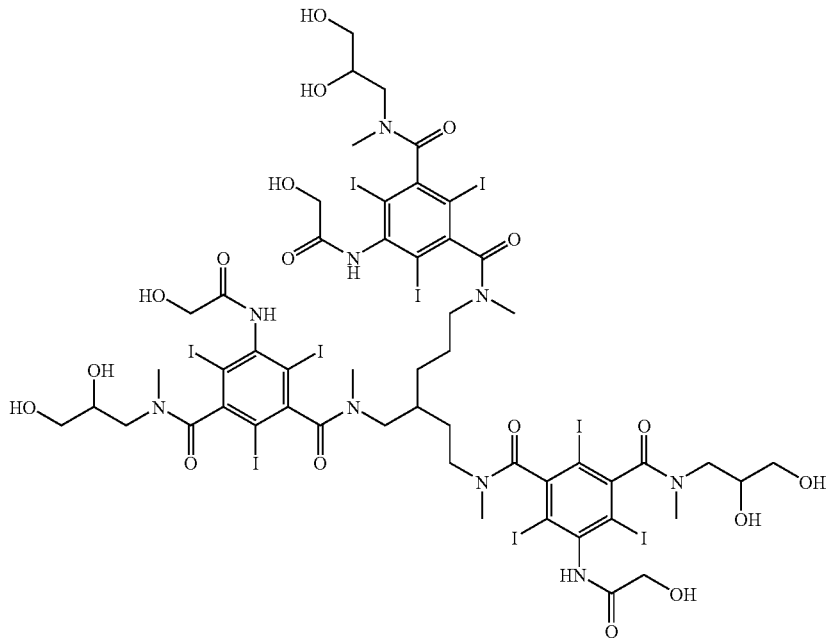

To a solution of acetic acid {3-chlorocarbonyl-5-[(2,3-dihydroxy-propyl)-methyl-carbamoyl]-2,4,6-triiodo-phenyl-carbamoyl}-methyl ester in DMA is added 0.3 equivalent of N1,N6-dimethyl-3-methylaminomethylhexane-1,6-diamine and 0.3 equivalent of triethylamine. The reaction is stirred at ambient temperature until the reaction proceeds no further. The reaction mixture is extracted into ethyl acetate and washed with water to remove the DMA. The organic layer is dried over MgSO4 and the filtrate is concentrated under vacuum to give the desired compound which is used in the next step without purification. The crude material was dissolved in the minimum amount of methanol and treated with aqueous ammonia. The reaction was stirred at ambient temperature and monitored by LC-MS. Whereupon, the reaction mixture is concentrated to dryness, dissolved in the minimum amount of water, filtered and purified by preparative HPLC to give the desired final product. The structure is confirmed by LC-MS

What is claimed is:

1. Compounds of formula (I)

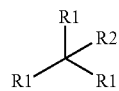

Formula (I)

wherein
each $R^1$ independently are the same or different and denote a moiety —$(CX_2)_n$—$R^3$—R;
$R^2$ denotes a hydrogen, a hydroxyl group or a $C_1$-$C_4$ alkyl group where the alkyl group may be substituted by hydroxyl or amino groups and interrupted by an oxygen atom;

each $R^3$ independently are the same or different and denote a moiety of formula —$NR^5$—CO— wherein $R^5$ has the meaning of $R^2$;
X denotes hydrogen or hydroxyl;
n is a integer of 1 to 4; and
each R independently are the same or different and denote a triiodinated phenyl group, further substituted by two $R^4$ groups wherein each $R^4$ are the same or different and denote a hydrogen atom or a non-ionic hydrophilic moiety, provided that at least one $R^4$ group in the compound of formula (I) is a hydrophilic moiety;
and salts or optical active isomers thereof.

2. Compound as claimed in claim 1 wherein X denotes a hydrogen atom.

3. Compound as claimed in claim 1 wherein each $R^5$ denote a hydrogen atom.

4. Compound as claimed in claim 1 wherein each n are the same or different and denotes the integers of 1, 2 or 3.

5. Compound as claimed in claim 1 wherein $R^2$ denotes hydrogen or methyl.

6. Compound as claimed in claim 5 wherein $R^2$ denotes a hydrogen atom.

7. Compound as claimed in claim 1 wherein each R are the same or different and denote a 2,4,6 triiodinated phenyl group, further substituted by two groups $R^4$.

8. Compounds as claimed in claim 1 wherein each $R^4$ are the same or different and denote a non-ionic hydrophilic moiety comprising esters, amides and amine moieties, optionally further substituted by a straight chain or branched chain $C_{1-10}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

9. Compounds as claimed in claim 8 wherein $R^4$ are the same or different and denote a non-ionic hydrophilic moiety comprising esters, amides and amine moieties, optionally further substituted by a straight chain or branched chain $C_{1-5}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

10. Compounds as claimed in claim 9 wherein $R^4$ are the same or different and denote a non-ionic hydrophilic moiety comprising esters, amides and amine moieties, further substituted by a straight chain or branched chain $C_{1-5}$ alkyl groups substituted by 1 to 3 hydroxy groups.

11. Compounds as claimed in claim 10 wherein each $R^4$ are the same or different and are polyhydroxy $C_{1-5}$ alkyl, hydroxyalkoxyalkyl with 1 to 5 carbon atoms and hydroxy-polyalkoxyalkyl with 1 to 5 carbon atoms attached to the iodinated phenyl group via an amide or a carbamoyl linkage.

12. Compounds as claimed in claim 1 wherein each $R^4$ are the same or different and are selected from groups of the formulas —CON($CH_3$)$CH_2$—CHOH—$CH_2$OH
—CONH—$CH_2$—$CH_2$—OH
—CONH—$CH_2$—CHOH—$CH_2$—OH
—CONH—CH—($CH_2$—OH)$_2$
—CON—($CH_2$—$CH_2$—OH)$_2$
—$CONH_2$
—$CONHCH_3$
—$NHCOCH_2$OH
—N($COCH_3$)H
—N($COCH_3$)$C_{1-3}$ alkyl
—N($COCH_3$)— mono, bis or tris-hydroxy $C_{1-4}$ alkyl
—N($COCH_2$OH)— hydrogen, mono, bis or tris-hydroxy $C_{1-4}$ alkyl
—N(CO—CHOH—CH2OH)— hydrogen, mono, bis or trihydroxylated $C_{1-4}$ alkyl
—N(CO—CHOH—CHOH—CH2OH)— hydrogen, mono, bis or trihydroxylated $C_{1-4}$ alkyl
—N($COCH_2$OH)$_2$
—CON ($CH_2$—CHOH—$CH_2$—OH) ($CH_2$—$CH_2$—OH)
—CONH—C ($CH_2$—OH)$_3$ and
—CONH—CH ($CH_2$—OH) (CHOH—$CH_2$—OH).

13. Compounds as claimed in claim 12 wherein each $R^4$ are the same or different and are selected from groups of the formulas —CONH—$CH_2$—CHOH—$CH_2$—OH, —CONH—CH—($CH_2$—OH)$_2$, —CON—($CH_2$—$CH_2$—OH)$_2$, —CONH—$CH_2$—CHOH—$CH_2$—OH, —$NHCOCH_2$OH and —N($COCH_2$OH)— mono, bis or tris-hydroxy $C_{1-4}$ alkyl.

14. Compounds as claimed in claim 1 wherein each $R^4$ are equal.

15. Compounds as claimed in claim 1 of formula (II)

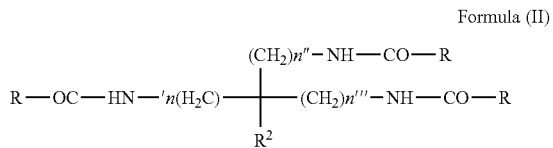

Formula (II)

wherein each group R are the same, $R^2$ denotes a hydrogen or a methyl group and n', n" and n''' are the same or different and denotes integers of 1, 2 or 3.

16. Compounds as claimed in claim 1 being N, N', N"-Tris-{2,4,6-triiodo-3[N-methyl-N-(2,3-dihydroxypropyl)aminocarbonyl]-5-(2,3,4-trihydroxy-butyrylamino)phenyl}-carbamoylethyl methane;

N, N', N"-Tris-{2,4,6-triiodo-3[N-methyl-N-(2,3-dihydroxypropyl)aminocarbonyl]-5-(2,3-dihydroxy-butyrylamino)phenyl}-carbamoylethyl methane;

N,N',N"-Tris-[(3(N-methyl-2,3-dihydroxypropylcarbamoyl)-2,4,6-triiodo-(2,3-dihydroxy -propionylamino) phenyl) carbamoyl methyl ethane;

N,N',N"-Tris-[(3(N-2,3-dihydroxypropylcarbamoyl)-2,4,6-triiodo-(2,3,4-trihydroxy -butyrylamino) phenyl) carbamoyl methyl ethane; and N1,N6-Bis-[2-(N-(2,3-dihydroxy-propyl)-5-(2-hydroxy-acetylamino)-2,4,6-triiodo-isophthalylamino) -hexyll]-N4'-(2,3-dihydroxy-propyl)-5-(2-hydroxy-acetylamino)-2,4,6-triiodo-isophthalamide.

17. An X-ray diagnostic composition comprising a compound of formula (I) as defined in claim 1 together with a pharmaceutically acceptable carriers or excipients.

18. A method of imaging, specifically X-ray imaging, comprising administration of compounds of formula (I) as defined in claim 1 to the human or animal body, examining the body with a diagnostic device and compiling data from the examination and optionally analysing the data.

19. A process for the production of compounds according to claim 1 wherein a reactive form of R, or a precursor thereof and/or R having optionally protected groups $R^4$ is reacted with an alkyl triamine group and the precursor group are further functionalised to form $R^4$ groups and/or protected $R^4$ substituents are deprotected.

20. N(3-allylcarbamoyl-5-chlorocarbonyl-2,4,6-triiodo-phenyl)-1-acetoxy acetamide.

* * * * *